US009931396B2

(12) United States Patent
Vanderplasschen

(10) Patent No.: US 9,931,396 B2
(45) Date of Patent: Apr. 3, 2018

(54) KOI HERPESVIRUS VACCINE

(71) Applicant: GESVAL, S.A., Angleur (BE)

(72) Inventor: Alain Vanderplasschen, Liege (BE)

(73) Assignee: GESVAL S.A., Angleur (BE)

( * ) Notice: Subject to any disclaimer, the term of this patent is extended or adjusted under 35 U.S.C. 154(b) by 0 days.

(21) Appl. No.: 15/164,010

(22) Filed: May 25, 2016

(65) Prior Publication Data

US 2017/0028057 A1 Feb. 2, 2017

Related U.S. Application Data

(63) Continuation of application No. 14/368,093, filed as application No. PCT/EP2012/076496 on Dec. 20, 2012, now abandoned.

(30) Foreign Application Priority Data

Dec. 30, 2011 (EP) .................................... 11196171

(51) Int. Cl.
*A61K 39/245* (2006.01)
*C12N 7/00* (2006.01)
*A61K 39/12* (2006.01)
*A61K 39/00* (2006.01)

(52) U.S. Cl.
CPC ............ *A61K 39/245* (2013.01); *A61K 39/12* (2013.01); *C12N 7/00* (2013.01); *A61K 2039/5254* (2013.01); *A61K 2039/5256* (2013.01); *A61K 2039/552* (2013.01); *C12N 2710/16021* (2013.01); *C12N 2710/16022* (2013.01); *C12N 2710/16034* (2013.01); *C12N 2710/16043* (2013.01); *C12N 2710/16051* (2013.01); *C12N 2710/16062* (2013.01); *C12N 2800/204* (2013.01)

(58) Field of Classification Search
CPC .. A61K 39/12; A61K 2039/53; A61K 39/245; A61K 2039/552; A61K 2039/5254; A61K 2039/6075; A61K 2039/525; A61K 2039/5258; A61K 35/76; A61K 35/763; C12N 2710/16034; C12N 15/86; C12N 2710/16022; C12N 2710/16043; C12N 2710/16062; C12N 2710/16021; C12N 2710/16051; C12N 2710/16171; C07K 14/005
See application file for complete search history.

(56) References Cited

FOREIGN PATENT DOCUMENTS

| | | | |
|---|---|---|---|
| EP | 0996738 | B1 | 2/2006 |
| WO | WO 2004/061093 | A1 | 7/2004 |
| WO | WO 2009/027412 | A1 | 3/2009 |

OTHER PUBLICATIONS

Waltzek TB, Kelley GO, Stone DM, Way K, Hanson L, Fukuda H, Hirono I, Aoki T, Davison AJ, Hedrick RP. Koi herpesvirus represents a third cyprinid herpesvirus (CyHV-3) in the family Herpesviridae. J Gen Virol. Jun. 2005;86(Pt 6):1659-67.*

Aoki, T., et al., 2007, "Genome sequences of three koi herpesvirus isolates representing the expanding distribution of an emerging disease threatening koi and common carp worldwide," Journal of Virology, vol. 81, pp. 5058-5065.

Costes, B., et al., 2008, "Cloning of the Koi Herpesvirus Genome as an Infectious Bacterial Artificial Chromosome Demonstrates that Disruption of the Thymidine Kinase Locus Induces Partial Attenuation in Cyprinus carpio koi," Journal of Virology, vol. 82, pp. 4955-4964.

Dewals, B., et al. 2006, "Cloning of the genome of Alcelaphine herpesvirus 1 as an infectious and pathogenic bacterial artificial chromosome," Journal of General Virology, vol. 87, pp. 509-517.

PCT International Search Report, International Filing Date Dec. 20, 2012; International Application No. PCT/EP2012/076496, dated Feb. 22, 2013.

PCT International Written Opinion, International Filing Date Dec. 20, 2012; International Application No. PCT/EP2012/076496, dated Feb. 22, 2013.

Messerle, M., et al., 1997, "Cloning and mutagenesis of a herpesvirus genome as an infectious bacterial artificial chromosome," Proceedings of the National Academy of Sciences, vol. 94, pp. 14759-14763.

Rakus, K. L., et al., 2012, "Gene expression analysis of common carp (*Cyprinus carpio* L.) lines during Cyprinid herpesvirus 3 infection yields insights into differential immune responses," Developmental & Comparative Immunology, vol. 37, pp. 65-76.

Wagner, M., et al., 2002, "Herpesvirus genetics has come of age," Trends in Microbiology, vol. 10, pp. 318-324.

Warming, S., et al., 2005, "Simple and Highly efficient BAC recombineering using galK selection," Nucleic Acids Research, vol. 33, e36.

Boutier, M. et al., 2015, "Rational development of an attenuated recombinant cyprinid herpesvirus 3 vaccine using prokaryotic mutagenesis and in vivo bioluminescent imaging," PLoS Pathogens, vol. 11, e1004690.

Gomez-Casado et. al., 2011, "A comparative review on European-farmed finfish RNA viruses and their vaccines," Vaccine, vol. 29, pp. 2657-2671.

KoVax. "KV3 Vaccine against KHV,." http://www.kovax.co.il/. Updated Mar. 27, 2014.

Borst, E. M., et al., 1999, "Cloning of the human cytomegalovirus (HCMV) genome as an infectious bacterial artificial chromosome in *Escherichia coli:* a new approach for construction of HCMV mutants," Journal of Virology, vol. 73, pp. 8320-8329.

Genbank Accession No. NC_009127, Cyprinid herpesvirus 3, complete genome, VRL Mar. 19, 2012.

Babic, N., et al., 1996, "Glycoprotein gH of pseudorabies virus is essential for penetration and propagation in cell culture and in the nervous system of mice," The Journal of General Virology, vol. 77, pp. 2277-2285.

(Continued)

*Primary Examiner* — Rachel B Gill
(74) *Attorney, Agent, or Firm* — Kelly M. Sullivan

(57) ABSTRACT

The present invention relates to a recombinant Koi herpesvirus (KHV), methods for the production of such KHV, cells comprising such KHV and the use of such KHV as vector and in vaccines for the prevention and/or therapeutic treatment of a disease in fish caused by Koi herpesvirus in carp such as *Cyprinus carpio carpio* or *Cyprinus carpio koi.*

15 Claims, 18 Drawing Sheets

(56) References Cited

OTHER PUBLICATIONS

Figure 1:
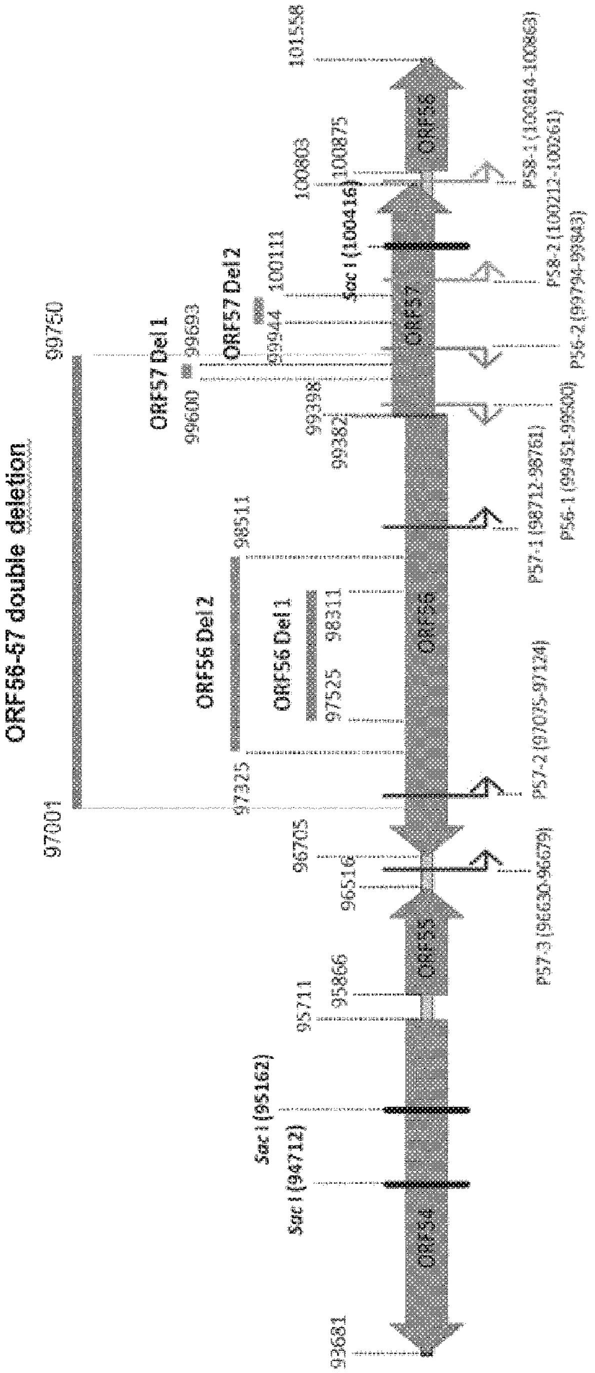

Schroder, C., et al., 1999, "Bovine herpesvirus 1 requires glycoprotein H for infectivity and direct spreading and glycoproteins $gH_{w450}$ and gB for glycoprotein D-independent cell-to-cell spread," The Journal of General Virology, vol. 80, pp. 57-61.
Gillet, L., et al., 2005, "Development of bovine herpesvirus 4 as an expression vector using bacterial artificial chromosome cloning," The Journal of General Virology, vol. 86, pp. 907-917.
Bovarnick, M. R., et al., 1950, "The influence of certain salts, amino acids, sugars, and proteins on the stability of rickettsiae." Journal of Bacteriology, vol. 59, p. 509-522.
"Remington: the science and practice of pharmacy" (2000, Lippincot, USA, ISBN: 683306472).
"Veterinary Vaccinology" (P. Pastoret et al. ed., 1997, Elsevier, Amsterdam, ISBN: 0444819681).
Neukirch, M., et al., 1999, "Isolation of a virus from Koi with altered gills," Bull. Eur. Ass. Fish. Pathol. vol. 19, pp. 221-224.
Hedrick, R. P., et al., 2005, Initial isolation and characterization of a herpes-like virus (KHV) from Koi and common carp. Bull. Fish. Res. Agen. Supplement 2, pp. 1-7.
Ilouze, M., et al., 2006, "Characterization of a novel virus causing a lethal disease in Carp and Koi," Microbiology and Molecular Biology Reviews, vol. 70, pp. 147-156.
Markine-Goriaynoff, N., et al., 2004, "The core 2 beta-1,6-N-acetylglucosaminyltransferase-M encoded by bovine herpesvirus 4 is not essential for virus replication despite contributing to post-translational modifications of structural proteins," Journal of General Virology, vol. 85, pp. 355-367.
Morgan, R. W., et al., 1990, "Transfection of chicken embryo fibroblasts with Marek's disease virus DNA," Avian Diseases, vol. 34, pp. 345-351.
Ronen, A., et al., 2003, "Efficient vaccine against the virus causing a lethal disease in cultured Cyprinus carpio," Vaccine, vol. 21, pp. 4677-4684.
Warden, C., et al., 2011. Herpesvirus BACs: past, present, and future. Journal of biomedicine & biotechnology, vol. 2011, Article ID 124595, 16 pages.

* cited by examiner

FL BAC excised ORF57 Del 1 galK strain

FL BAC excised ORF57 Del 2 galK strain

FL BAC excised ORF56 Del 1 galK strain

FL BAC excised ORF56 Del 2 galK strain

FL BAC excised strain

FL BAC excised ORF56-57 Del strain

FL BAC revertant ORF56-57 Del strain

Mock-infected

SEQUENCE LISTING

```
<160> NUMBER OF SEQ ID NOS: 12

<210> SEQ ID NO 1
<211> LENGTH: 77
<212> TYPE: DNA
<213> ORGANISM: Koi Herpesvirus

<400> SEQUENCE: 1

cgtacagggt ggcggtgcac ctgtcccaga aggccttcac cgcctgggag ctccctgttg     60

acaattaatc atcggca                                                    77


<210> SEQ ID NO 2
<211> LENGTH: 71
<212> TYPE: DNA
<213> ORGANISM: Koi Herpesvirus

<400> SEQUENCE: 2

cggctcatca tctgcgggtc catccaggcg cccttgcccc acagcagagc ttcagcactg     60

tcctgctcct t                                                          71


<210> SEQ ID NO 3
<211> LENGTH: 74
<212> TYPE: DNA
<213> ORGANISM: Koi Herpesvirus

<400> SEQUENCE: 3

ctttgtgctg cacaagggct tcaaccacca ctacgccttc tgcgatcacc cctgttgaca     60
```

-continued attaatcatc ggca 74

<210> SEQ ID NO 4
<211> LENGTH: 74
<212> TYPE: DNA
<213> ORGANISM: Koi Herpesvirus

<400> SEQUENCE: 4
ctgagcgttg ttgaaggcct ccatcaggtg ctgcctgatc tgcttgtgca gagctcagca 60
ctgtcctgct cctt 74

<210> SEQ ID NO 5
<211> LENGTH: 74
<212> TYPE: DNA
<213> ORGANISM: Koi Herpesvirus

<400> SEQUENCE: 5
tcaggatcga ggtcaccagc ttgagcttct cgggcatgta ctcgcgccac cctgttgaca 60
attaatcatc ggca 74

<210> SEQ ID NO 6
<211> LENGTH: 70
<212> TYPE: DNA
<213> ORGANISM: Koi Herpesvirus

<400> SEQUENCE: 6
cggcgaggtg atttcggtca tgagcaaatc gattgcggcc gaacagcagc tcagcactgt 60
cctgctcctt 70

<210> SEQ ID NO 7
<211> LENGTH: 74
<212> TYPE: DNA
<213> ORGANISM: Koi Herpesvirus

<400> SEQUENCE: 7
gatcgggtac gtcggcgtgc gccacttgac cttcctcaac gtccccgtca cctgttgaca 60
attaatcatc ggca 74

<210> SEQ ID NO 8
<211> LENGTH: 70
<212> TYPE: DNA
<213> ORGANISM: Koi Herpesvirus

<400> SEQUENCE: 8
gcgcacacca tcaccatctg tcccatgtct ccccaacgct acaccgtgac tcagcactgt 60
cctgctcctt 70

<210> SEQ ID NO 9
<211> LENGTH: 70
<212> TYPE: DNA
<213> ORGANISM: Koi Herpesvirus

<400> SEQUENCE: 9
gtccctcgac agccccagcc cgcacagcag tcgccactct tccctgttga tcagcactgt 60
cctgctcctt 70

<210> SEQ ID NO 10
<211> LENGTH: 74
<212> TYPE: DNA
<213> ORGANISM: Koi Herpesvirus

<400> SEQUENCE: 10
aacccgtaca cgacgcgctc aagcagcttg atcttgacga cgtcgtgcac cctgttgaca 60
attaatcatc ggca 74

<210> SEQ ID NO 11
<211> LENGTH: 499
<212> TYPE: DNA
<213> ORGANISM: Koi Herpesvirus

<400> SEQUENCE: 11
tttgtcaacc agtcctccag ggtcggtttg gcgctggcct ccttgccctt ggtcacggcg 60
atggcagacg ccacaatcct cgcgacgggt tccgtcagag cagagttctt aaacatttcg 120
acgcctcctc cgacggtgaa ccactctgac caattcaggt cggagggcca cgtctgcctg 180
tgcatcatcg tctgcacagc gtccctcgac agccccagcc cgcacagcag tcgccactct 240
tccctgttga gtgcacgact cgtcaagatc aagctgcttg agcgcgtcgt gtacgggttc 300
atgatggccc tgcagaaggc gctgcgcatt cagaagcagg gctgcaggat ggtggggctc 360
gaggacccgg agaaggtgga ggatatgaag aactttgtgc tgcacaaggg cttcaaccac 420
cactacgcct tctgcgatca ccactggcag cactgggccc tgggccgctc cttcgagggc 480
gagctgcccg acgtggtgg 499

<210> SEQ ID NO 12
<211> LENGTH: 4929
<212> TYPE: DNA
<213> ORGANISM: Koi Herpesvirus

<400> SEQUENCE: 12
ccaatacttt aaaaaaaaca ggagatatta aatatagttc aaacgtttat tgggatacac 60
acatcataca caaaatcatg tgctcaacag ttcgacgggg atggagcccg tgtgtccgta 120
ctttgtcaac cagtcctcca gggtcggttt ggcgctggcc tccttgccct tggtcacggc 180
gatggcagac gccacaatcc tcgcgacggg ttccgtcaga gcagagttct taaacatttc 240
gacgcctcct ccgacggtga accactctga ccaattcagg tcggagggcc acgtctgcct 300
gtgcatcatc gtctgcacag cgtccctcga cagccccagc ccgcacagca gtcgccactc 360
ttccctgttg agcggcacga acgccaacgc gtcgcacccc accgtcgagg ccagcatctc 420
cgagtacatt agcgacgtct ggtcctcctg ggtaaagagg cgggtgggca cgttctcggc 480
gaagcacctc atcagcacgg tccccacggc gtgcctaaag ttttggtagg gctgcttcat 540
gtacatcttg aaaacggcgt aggcctcgtc gattgtcaca tgctggtcca ggcgcgtgtt 600
gatggcaaag atggcctggt acaagacggc ctgctgcggg tcctcgatcg ggtacgtcgg 660
cgtgcgccac ttgaccttcc tcaacgtccc cgtcatggaa gcctcgcagg gcatgtagtc 720
gacggcgcac ttgggcacga tgctcttgat ctgttccaca ctcaggcccc tgatggtgcc 780
caggttgggc agcgcgttga tgaccctggc gaagcccgtc gccgccttca gcttggggtt 840
gacgctcagg atcgaggtca ccagcttgag cttctcgggc atgtactcgc gccacagaaa 900
gagctgcgag cagctcgcgc cgttcagaaa gctcagcatg ttcttggggt agtgcagcct 960
gaggtccacc acgttccagc tgctgtgcga cccgttcgtc accacctgct ccagagtcgt 1020
accgctcatc atgtagtgca ggatgctcgc gtggtacttg ttggcgtaca tggcaatgtc 1080
cagcaggcag gccttggcac tcaccgtgca agaatcgagc aggcaccgcg acatcctctg 1140

-continued

```
gcacatcatg tcactcgact ctagcaccgt tctcacgtag atgtacgagc ggcaggtcat   1200
gggccgactc atcaccgtcg cgacggccac cacgttctgc tgcaccatct tcatcagctc   1260
catcacgcct ttggtcttgt ggtagtcgtc ccacacgtag tggcagacca cgtcctgcag   1320
aaactcgcag tccgatagca gctccctgaa gtgggaccgg agcacccgcg tcctgaaccc   1380
ggccgcgcac gtcgcgcagt tcagcagcgc gatgtgctcc tcgctctggt cgcacttgcg   1440
gtgggtcgga ttcggcttgg gtgccgtctc tgccgccgcc ttcaacgcgg gtaccttgag   1500
gtgctgctga caaccgggtg gcctgacccg agtctgagga gtctgagtct tctgcggagg   1560
gtactgcgcc ttgggaacgt agatgtgagg gtgtgagagg tgagggtgcg ggtacggcgg   1620
cggtggcagc accagcgtct tgcctccctc gatggtgatg gtcagcttct tgggctgctg   1680
ctgctgctgt tcggccgcaa tcgatttgct catgaccgaa atcacctcgc cgtcgtcctc   1740
atcagcctcg tcgtccgcat cgacttccat cctctcattc tcggccctca ccttctcccc   1800
cctctctacg acccccgagg cggaggaggt ggtagtggtg gtgcctgagg aggacgcggt   1860
ggaggtgatc agcggagtct ccgtcacggt gtagcgttgg ggagacatgg gacagatggt   1920
gatggtgtgc gccgtcgtgt gaggcggcag cacggcgagg agcttgggag gctgaggttt   1980
ggccgcctcc ggcgcggccc tcctgaagac gcccgtctca aagttgacgg gcggcgtgtc   2040
caccatcacg ttcacgatgg ggttcctctt ggcgaaggac agaggcgccg gcctctgcgc   2100
cgcgatggtc cacaccggcg gcaacatcct attgttgacg acggtgtccg aggcggatga   2160
cacggacatg cacctgctca gggtccaggc cctgagcatg gccctggacc cctcgtgctt   2220
gctggtgctg gtggtgccgc cgctgcctga cacgctcaga ttctcgggct cgtcaaccgt   2280
ctccacatca atctcgtcct cctcatccgc cagggccgag acggcggccg agacggcggc   2340
ggctgtagcc gaccggctgt tgctgcgcgt gtaggggtga tgcctctgcg tcttcttgtt   2400
gaagatgtgc tccgagacgt gtttgttcga gatctcgatc tgctcctcga tctccttgta   2460
cgagatcggc tttcggcgac ggcggcccct gccgaggcga gtcggcaccg gactcgtgtc   2520
gatgaccagg ttctcgtgat catcttcttc ctcggtccgt ttaccgtcgt cggggacggg   2580
tacggggttg ggtacggggt tggcgacctc gccatcattt tcgttggcgt ttgcgttggt   2640
agacatgata ttggcaaatt ttcggtctct ctgcgctaac ggagttgtgt gtgacgaggg   2700
gtgaccccga aggttcatat tccccctcga ctgggtgcga ccgcagcgcc tgatggcagc   2760
cagggacatt gcgatgaatc agcggggtgc tgcgggtgat ggcggcgagg acgaggaatc   2820
gaccttcgac aacagctgcg aggatctgcc cgactttgta gaggcctgcc tgacggagga   2880
gaaccgcaag cggtacaaca tccaggacgg cgactttcct ccgtacaggg tggcggtgca   2940
cctgtcccag aaggccttca ccgcctggga cgaggtcgac tacgcggccc tggccgactg   3000
cctgtgcgag ggtacccacc tgcaggccgt gcacactcac aagctctacg tgctggcgtg   3060
cggcgctctg ctgtggggca agggcgcctg gatggacccg cagatgatga gccgtctcta   3120
cgtgcacgac gtcgtcaaga tcaagctgct tgagcgcgtc gtgtacgggt tcatgatggc   3180
cctgcagaag gcgctgcgca ttcagaagca gggctgcagg atggtggggc tcgaggaccc   3240
ggagaaggtg gaggatatga agaactttgt gctgcacaag ggcttcaacc accactacgc   3300
cttctgcgat caccactggc agcactgggc cctgggccgc tccttcgagg gcgagctgcc   3360
cgacgtggtg gtcaaggaga tgattagcga cggcctagcc tgcaccctgg agcgcgccgg   3420
tcccttctcg acgctggccg actggctcga gtccttcagt ctccgcgcct acccgcagcc   3480
catgcacaag cagatcaggc agcacctgat ggaggccttc aacaacgctc aggacgtcga   3540
```

-continued

```
ctttccgatg ttcaagagca gcctcaagtt cctggcctcg atgcactgcc tctacaagac   3600

gccgcgctgg agcttcatgc ccagcgccgt caataccacc ctcgacacct tcgacgactg   3660

cgcctgcgac gtgcacgtcc tgcgccacgt cgagggccaa aacagctgcg actgtctgtg   3720

ctgccgtcgc cagggctgtc acgacgagga ctgccgtccc accgcggccc tggacgcggc   3780

cgagctccgc ggcgagggca tgtcggacga cgacgacatc gagagcgagg aggaggccct   3840

cggcgccgtc aagctggacg tgggccgcat gaagcagaag cgcatgcaga aggccatgcg   3900

ctacgcctcg gcagctgcgg cagccgacgc cgcggacggt cagaagatgt actccgtcaa   3960

agagcccaag gtggtggccg tcaaggctca gctggtgggt gtcggcgata ccgacgctcc   4020

ctcatcctcc acggcggcaa aggactgcgc ggacggcaag tgtcagggac cctgcaactg   4080

cgagcgtcct cccggccctc cgaccgacta cgacaagagg gttaaggcca agaagatcag   4140

gaagcccaag aacctaccca aaaccaaatc ctaacatctc gctcactcac tcaccaataa   4200

aaaaagtcag agtctagtat tgttagtgtg tgtttttatt gtttcatgtt tcaaacaagt   4260

acgacagtga aagagttaac aaaatgtgat cggaggttcg ttggtgatct gaaccgtccc   4320

ccacaacgtg aggatgtgtg tggacgagcc gtcgcggggc tcgccgctca tcacgtccca   4380

cacgagtcgc cggtcctagt cccgcttctg agcccaggcg agccgtctgg tcgaacggtt   4440

cccaacggcg acgtctaccg gtctgaggga ccagggtccg cggccggttg cgctcgcccg   4500

ctctgcgggt caggcggtca cccagaggac gtctggagcg ggttttcggc gacggtccgg   4560

ggtcgaccgt ctctgcacga tccgcgagtg ggtaggcagc gctggcccga gccgtccgtc   4620

tcgacgtgcc cgcaggtacc tccaagccga gacggcgacg gcgagcaacc tcggtcgacg   4680

ccgacctacc ccgttgccgg ggtgcaggtc agaggggctc tcacctccct ccttcccacg   4740

cggccgacgg cgtccgaagc cgtctcatca tcaaccgttc atcggacgaa ggcgtcccgc   4800

ggaacgctgc cgagcgtgga ccgccgggga taccaacgcc gtgaccctgc cgactcgcga   4860

accgtcagag gccggtgggg attcccgtgc cgagcgcctt cccttcctcc ggacgcctgt   4920

ctctggtag                                                           4929
```

KOI HERPESVIRUS VACCINE

This application is a continuation of U.S. application Ser. No. 14/368,093, which is a national stage 371 application of the international application PCT/EP2012/076496, filed Dec. 20, 2012, which claims priority to the EP Application No. 1119617.0, filed Dec. 30, 2011, the contents of which are incorporated by reference in their entirety.

The present invention relates to a recombinant Koi herpesvirus (KHV), methods for the production of such KHV, cells comprising such KHV and the use of such KHV as a vector and in vaccines for the prevention and/or therapeutic treatment of a disease in fish caused by Koi herpesvirus in carp such as *Cyprinus carpio carpio* or *Cyprinus carpio koi*.

Common carp (*Cyprinus carpio carpio*) is the most widely cultivated fish for human consumption mainly in Asia, Europe, and the Middle East. In contrast, the Koi (*Cyprinus carpio koi*) subspecies is cultivated as a pet fish for personal pleasure or competitive showing especially in Japan but also worldwide. A virus causing a lethal disease in both common and Koi carp, initially called Koi herpesvirus disease (KHVD), was detected in 1996 in the United Kingdom. The virus was then rapidly identified as the cause of mass mortality among Koi and common carp in Israel, the USA, and Germany. Intensive culture of common carp, Koi shows and international trading have contributed to the rapid global spread of this highly contagious and extremely virulent disease. Since its emergence, KHVD has caused severe financial and economic losses in both Koi and common carp culture industries worldwide.

Initial characterization of the virus showed a herpes-like structure with an envelope and an icosahedral electron-dense core of 100-110 nm surrounded by a tegument-like structure. The genome of the virus comprises linear double-stranded DNA (dsDNA) of ~295 kb similar to that of Cyprinid herpesvirus 1 (CyHV-1) but larger than those of Herpesviridae members generally ranging from 125 to 240 kb in size. The sequence of KHV genome has been published quite recently (Aoki et al., J Virol, 81, pages 5058-5065 (2007)). The KHV genome contains a significant number of DNA sequences without homology to any other known viral sequences. Moreover, it contains highly divergent DNA sequences encoding polypeptides, which resemble those of several dsDNA viruses, like herpesvirus, poxvirus, iridovirus and other large DNA viruses.

The unique characteristics of this virus have led to three different nomenclatures: firstly, Koi herpesvirus (KHV) according to its morphological manifestation; secondly, carp interstitial nephritis and gill necrosis virus (CNGV) according to its pathogenic effects in fish; and lastly Cyprinid herpesvirus 3 (CyHV-3) according to gene content similarity with CyHV-1 and with CyHV-2. The latter nomenclature has been further supported by the recent sequencing of the full length of the viral genome. However, hereinafter the name KHV will be used.

KHV bears a genome of approximately 295 kb which represents the largest genome ever identified among Herpesvirales members. Although the first isolation of KHV dates from 1996, only little information is available about the role of individual genes in KHV pathogenesis and in the biology of the infection of the natural host.

An attenuated KHV and its potential use as a vaccine candidate has been described in the International Patent Application WO 2004/061093 A1. However, this vaccine candidate hides a potential danger. The attenuation is the consequence of random mutations that occurred during viral replication in vitro. Consequently, the character of the attenuation is unknown and reversion to a fully pathogenic phenotype can not be excluded.

Applied and fundamental research on KHV requires production of recombinant virus. Recently, manipulation of large herpesvirus genomes became feasible through the use of bacterial artificial chromosome (BAC) vectors (Messerle et al., Proc Natl Acad Sci USA, 94, 14759-14763 (1997); Wagner et al., Trends Microbiol, 10, 318-324 (2002) and vide infra). These vectors allow the maintenance and efficient mutagenesis of the viral genome in *Escherichia coli* (*E. coli*) followed by the reconstitution of progeny virions by transfection of the BAC plasmid into permissive eukaryotic cells. To date, the genomes of several herpesviruses have been successfully propagated as infectious BAC clones, including Human Cytomegalovirus (HCMV) which represents the second largest herpesvirus genome cloned as a BAC to date (230 Kb) (Borst et al., J Virol, 73, 8320-8329 (1999)).

Recently, several recombinant KHV have for the first time been constructed using the BAC technique; these recombinants are all described in PCT Patent Application WO2009/027412. This patent application discloses a method to make recombinant KHV's having a deficiency in one or more of the genes selected from the group consisting of ORF55: the thymidine kinase gene; ORF12: putative tumor necrosis factor (TNF) receptor gene; ORF16: putative G-protein coupled receptor (GPCR) gene; ORF134: putative Interleukin 10 homologue gene; ORF140: putative thymidylate kinase gene, or combinations thereof. Such mutants were used as live attenuated vaccine viruses.

It was shown that some of these mutants were safe when used in specific SPF fish of a certain size and age. However, in the field, fish farmers are interested in early vaccination, i.e. when the fish are relatively young/small and where there exists a relatively large spreading in size of the fish. It turned out that in such conditions vaccines based upon the deletion mutant viruses as disclosed in International Patent Application WO2009/027412 may in some situations not be sufficiently safe: such recombinant KHV are too virulent for use in young/small fish. This means that at present, there still is a lack of safe and efficacious attenuated recombinant vaccines for the control of the disease in field situations such as in fish farming.

It is an object of the present invention to provide novel recombinant KHV viruses that can be used for the development of safe and efficacious attenuated vaccines to control KHV infection in the field.

It was surprisingly found now that a recombinant KHV in which the Open Reading Frame 57 (ORF57) is deficient, shows a strongly reduced or no mortality at all, even in very young/small carp infected with this herpesvirus recombinant and provides immunity against wild-type Koi herpesvirus. Such a recombinant KHV thus provides a safe and efficacious attenuated vaccine virus that can suitably be used in young and/or small carp.

This finding is even more surprising in view of the fact that ORF57 was up till now thought to be an essential gene, without which no live virus would be feasible.

Therefore, a first embodiment of the present invention relates to a recombinant Koi herpesvirus in which ORF57 is deficient, resulting in a KHV which is attenuated and induces a mortality rate of 40% or less in carp, preferably *Cyprinus carpio carpio* or *Cyprinus carpio koi*, when infected with said herpesvirus.

As used herein, a "deficient" ORF57 is an ORF57 that is no longer functional, i.e. no longer capable of encoding a functional protein. A deficient ORF57 as used herein, results in a KHV which is attenuated to the level that it induces a mortality rate of 40% or less in carp. Such a deficiency can e.g. be obtained by mutation such as insertion or deletion of one or more nucleotides in the gene encoding ORF57, or in its promoter region. Such a mutation can e.g. be a frame shift mutation at the 5' site of the gene, or a deletion of (part of) the promoter region or (part of) the gene itself.

An example of the DNA sequence of ORF57 is the DNA sequence of ORF57 as given in Genbank accession N° NC_009127 where the ORF57 start and stop codon are located at position 99382 and 100803. It goes without saying that the location of ORF57 may differ in other KHV strains due to natural variation. Also, due to natural variation, there may be small differences in the sequence of ORF57 in one KHV strain when compared to another KHV strain. Therefore, the ORF57 as described herein, is an open reading frame having a sequence identity of more than 80% with the DNA sequence of ORF57 as given in Genbank accession N° NC_009127.

The nucleotide sequence of the region comprising ORF56, 57 and 58, spanning nucleotides 96630-101558 is represented in SEQ ID NO: 12. See also FIG. 1.

It is clear that the most extensive way of making a gene deficient, i.e. the deletion of the whole ORF57 will result in no ORF57 protein production at all.

From a practical point of view and from a point of safety, such a full deletion would be a logical step to take. However, as follows from FIG. 1, a putative promoter region is located at position 100212-100261 that may possibly be involved in the expression of the adjacent ORF58. For this reason, a mutation in ORF57 should preferably not extend into this region. Thus, it is preferred to introduce mutations in ORF57 in the region on the left hand of position 100212 or on the right hand of position 100261.

It can also be seen from FIG. 1 that two putative promoter regions are located at respectively position 99451-99500 and position 99794-99843 that may possibly be involved in the expression of the adjacent ORF56. It is therefore theoretically possible that a deletion in a region in ORF57 interferes with the expression of ORF56. In that case, it could be that a recombinant KHV in which ORF57 is deficient according to the invention merely behaves attenuated as a result of a lower expression of ORF56. It is however shown in the Examples section that 1) ORF56 is not an essential gene, and 2) a deficient ORF56 does not contribute to the attenuated character of the recombinant KHV according to the invention. In these Examples it is shown that large deletions can be made in ORF56 without influencing the viability of the recombinant KHV and without significantly changing the attenuated character of the recombinant KHV. This implies that the putative ORF56 promoter sites located in ORF57 can be removed without problems.

It follows also from FIG. 1, that two putative promoter sites for ORF57 are located in ORF56 at positions 97075-97124 and 98712-98761. Therefore, it could not be excluded that the deletion of a small part of ORF57, such as in ORF57 Del 1 provides a truncated but still functional ORF57-encoded protein. In order to exclude this possibility, a large ORF56-ORF57 double deletion was made as described in the Examples section that spans the region from position 97001-99750. This deletion behaves essentially equal to the single ORF57 mutants, as can be seen in FIG. 5 when compared with FIG. 7. Therefore it can be concluded that the ORF57-encoded protein is non-essential to the virus.

Deletion of only a small part of ORF57 is a possibility, it can even be a preferred possibility for the reasons given above, but some care has to be taken that the resulting truncated protein is non-functional. If the skilled person would for whatever reason decide to delete less than the full ORF57, he would easily be able to check if the ORF57 is made deficient: a non-deficient ORF57 would lead to a virus having too high a level of virulence, i.e. too low a level of attenuation.

Preferably, the recombinant KHV is additionally deficient in one or more viral genes which contribute(s) to virulence but is/are not essential for replication of the virus.

Thus, a preferred form of this embodiment relates to a recombinant Koi herpesvirus according to the invention which is deficient in at least one additional gene which contributes to virulence but is not essential for replication of the virus.

A more preferred form of this embodiment relates to a recombinant Koi herpesvirus according to the invention which is deficient in at least one additional gene which contributes to virulence wherein said gene is selected from the group consisting of thymidine kinase gene; ORF12: putative tumor necrosis factor (TNF) receptor gene; ORF16: putative G-protein coupled receptor (GPCR) gene; ORF134: putative Interleukin 10 homologue gene; ORF140: putative thymidylate kinase gene, or any combination thereof.

In an even more preferred form of this embodiment, the recombinant KHV is additionally deficient in at least the thymidine kinase gene or the putative thymidylate kinase gene.

In another even more preferred form of this embodiment, the recombinant KHV according to the present invention is additionally deficient in the thymidine kinase gene and at least one further gene which contributes to virulence selected from the group consisting of ORF12: putative tumor necrosis factor (TNF) receptor gene; ORF16: putative G-protein coupled receptor (GPCR) gene; ORF134: putative Interleukin 10 homologue gene or ORF140: putative thymidylate kinase gene.

In a still even more preferred form of this embodiment, the recombinant KHV is additionally deficient in at least the thymidine kinase gene and the putative thymidylate kinase gene.

In another preferred form of this embodiment, the recombinant Koi herpesvirus according to the present invention is in a live form. Preferably, the recombinant Koi herpesvirus has the capability to reconstitute infectious particles, i.e.; to replicate when introduced into permissive eukaryotic cells or fish individuals, preferably in carp, more preferably in *Cyprinus carpio*, even further preferred in *Cyprinus carpio carpio* and/or *Cyprinus carpio koi*.

In an alternative embodiment the recombinant KHV according to the present invention is additionally deficient in one or more viral genes which is/are essential for replication (and optionally deficient in one or more viral genes which contribute(s) to virulence but is/are not essential for replication of the virus), thus providing a recombinant Koi herpesvirus according to the invention in a non-replicative form.

Thus, an alternative embodiment relates to recombinant KHV according to the present invention wherein said herpesvirus is in a non-replicative form.

A "non-replicative form" means that the recombinant Koi herpesvirus still has the capability to infect cells or fish individuals (e.g. *Cyprinus carpio, Cyprinus carpio carpio* or *Cyprinus carpio koi*) but is not able to replicate to the extend that infective progeny virus is formed.

A non-replicative recombinant strain is produced by inactivation (by means of known techniques such as insertion, deletion or mutation, e.g. using BAC cloning) of a KHV gene that is essential for replication.

Such a deleted virus is cultured on a permissive cell line stably expressing the deleted gene (trans-complementation).

This approach is an approach well-known in the art. It has i.a. been used successfully for different herpesviruses such as gH deleted Suid Herpesvirus 1 (Aujeszky virus) (Babic et al, 1996) and Bovine Herpesvirus 1 (Schröder and Keil, 1999).

Any gene which contributes to replication may be made deficient in order to obtain a non-replicating recombinant Koi herpesvirus. In other words, any gene of which the inactivation leads to a non-replicative recombinant Koi herpesvirus, can be deleted. Preferably, a gene of the recombinant KHV according to the present invention that is deleted in order to provide a non-replicative form of the virus, is selected from the group consisting of: ORF25, ORF31, ORF32, ORF34, ORF35, ORF42, ORF43, ORF45, ORF51, ORF59, ORF60, ORF62, ORF65, ORF66, ORF68, ORF70, ORF72, ORF78, ORF81, ORF84, ORF89, ORF90, ORF92, ORF95, ORF97, ORF99, ORF108, ORF115, ORF131, ORF132, ORF136, ORF137, ORF148 and ORF149.

A recombinant Koi herpesvirus according to the present invention preferably comprises a bacterial artificial chromosome (BAC) vector sequence.

Since about one and a half decade, the manipulation of large herpesvirus genomes has been greatly facilitated by the use of such bacterial artificial chromosomes. These vectors allow the maintenance and the mutagenesis of the viral genome in *Escherichia coli*, followed by reconstitution of progeny virions by transfection of the BAC plasmid into permissive eukaryotic cells. In a first step, the sequences for the BAC vector are introduced into the herpesvirus genome by conventional homologous recombination in infected cells. The linear double-stranded DNA genome of herpesviruses circularizes during replication. It suffices to isolate the circular replication intermediate of the BAC mutant and to shuttle it by DNA transformation into *E. coli*. This shuttle is needed only once to establish the system. The herpesvirus BAC is then propagated and mutated in *E. coli*. The homogenous, clonal herpesvirus BAC DNA is shuttled back into eukaryotic permissive cells only for virus reconstitution. As viral functions are not required, the virus genome remains sleeping while in *E. coli*, preserving the viral functions present at the time of cloning. This is important for viruses where in vitro culture procedures change the authentic properties of isolates.

As used herein, the term "homologous recombination" indicates that when two different homologous nucleic acid molecules encounter each other, crossover occurs, and a new combination of nucleic acid is generated. As used herein, the term "sequence mediating homologous recombination" refers to a sequence which causes homologous recombination which is dependent from a specific recombination protein, which is catalyzing, carrying out or assisting in homologous recombination. Such a recombination protein preferably acts specifically on a "sequence mediating homologous recombination" and does not act on other sequences.

BAC vector sequences are well-known in the art and their use in the construction of recombinant viruses such as herpesviruses has frequently been described in the art (Borst, E. M., Hahn, G., Koszinowski, U. H. & Messerle, M. (1999), J Virol 73, 8320-9. Costes, B., Fournier, G., Michel, B., Delforge, C., Raj, V. S., Dewals, B., Gillet, L., Drion, P., Body, A., Schynts, F., Lieffrig, F., Vanderplasschen, A., 2008. J Virol 82, 4955-4964. Dewals, B., Boudry, C., Gillet, L., Markine-Goriaynoff, N., de Leval, L., Haig, D. M. & Vanderplasschen, A. (2006), J Gen Virol 87, 509-17. Gillet, L., Daix, V., Donofrio, G., Wagner, M., Koszinowski, U. H., China, B., Ackermann, M., Markine-Goriaynoff, N. & Vanderplasschen, A. (2005), J Gen Virol 86, 907-17. Messerle, M., Crnkovic, I., Hammerschmidt, W., Ziegler, H. & Koszinowski, U. H. (1997), Proc Natl Acad Sci USA 94, 14759-63. Warming, S., Costantino, N., Court, D. L., Jenkins, N. A. & Copeland, N. G. (2005), Nucleic Acids Res 33, e36. Wagner, M., Ruzsics, Z. & Koszinowski, U. H. (2002), Trends Microbiol 10, 318-24).

The BAC vector sequence need not necessarily be inserted into ORF57. Alternatively it can be inserted in any other viral gene which contributes to virulence and/or any other viral gene which is or isn't essential for viral replication and/or any intergenic region.

However, in a more preferred form, the recombinant Koi herpesvirus comprises a BAC vector sequence which is inserted into ORF57. Such insertion has the advantage that by inserting the BAC vector into ORF57, ORF57 becomes at the same time deficient, thus directly providing a recombinant KHV according to the invention.

An example of a recombinant KHV according to the present invention was achieved by cloning of the KHV genome by the insertion of a modified loxP-flanked BAC cassette into ORF55 (vide infra). This insertion led to a BAC recombinant virus whose genome was stably maintained in bacteria and was able to regenerate virions when transfected into permissive cells. (See: Costes, B., Fournier, G., Michel, B., Delforge, C., Raj, V. S., Dewals, B., Gillet, L., Drion, P., Body, A., Schynts, F., Lieffrig, F., Vanderplasschen, A., 2008, J Virol 82, 4955-4964 for BAC-vector details, and vide infra for technical details). This vector was used to introduce a deletion in ORF57.

The term "BAC vector" refers to a plasmid which is produced using F plasmid of *E. coli* and a vector which can stably maintain and grow a large size DNA fragment of about 300 kb or more in bacteria, such as *E. coli* and the like. The BAC vector contains at least a BAC vector sequence essential for the replication of the BAC vector. Examples of such a region essential for replication include, but are not limited to, the origin of replication of F plasmid and variants thereof.

As used herein, the term "BAC vector sequence" refers to a sequence comprising a sequence essential for the function of a BAC vector. Optionally, the BAC vector sequence may further comprise a "recombination protein-dependent recombinant sequence" and/or a "selectable marker".

Details of i.e. "recombination protein-dependent recombinant sequence" and/or a "selectable marker" are given e.g. in the literature referred to above, and in WO 22009/027412.

Regardless the place where the BAC vector is inserted in the genome, it is preferred that the BAC vector sequence is flanked by sequences mediating homologous recombination, preferably loxP. Also, preferably the BAC vector sequence comprises a selectable marker (vide infra). In a more preferred form, the selectable marker is a drug selectable marker (vide infra).

In another preferred embodiment the genome of said recombinant herpesvirus is present in the form of a plasmid. This is achieved by isolating circular forms of the above mentioned recombinant Koi herpesvirus comprising a BAC vector sequence and introduction into bacterial cells. As mentioned above, it is not essential for the invention that the BAC (bacterial artificial chromosome) vector sequence is inserted into one or more of the viral genes which contribute to virulence or are necessary for replication, as long as one or more of the mentioned genes which contribute to virulence or are necessary for replication is/are made deficient by genetic engineering techniques.

Therefore, the BAC vector sequence may be inserted into any region of the virus genome, provided that ORF57 and preferably one or more other viral genes which contribute to virulence are also deficient.

Of course, the use of BAC vector mediated cloning techniques as described above can be used repeatedly: e.g. a first time to make ORF57 deficient and a second time to make an additional gene deficient.

The BAC vector sequence may in principle remain present in a recombinant KHV according to the invention in further applications without problems. However, for the use of a Koi herpesvirus according to the invention in e.g. a vaccine, it is preferred that most of the BAC sequences are removed. This is e.g. the case for BAC sequences that comprise genes encoding the selectable markers and even more for resistance genes. The presence of such genes in a vaccine is not only considered unnecessary, but even undesirable.

Thus, preferably at least a part (e.g. a part that comprises a resistance gene or a selectable marker), or more preferably most of the BAC vector sequence is excised from the herpesvirus genome, thereby preferably leaving behind a heterologous sequence at the excision site or former insertion site in the herpesvirus genome. More preferably, the heterologous sequence has a size of less than 200 nucleotides. The excision is achieved by introduction of the recombinant KHV into a permissive eukaryotic cell expressing the Cre recombinase which is excising the loxP-flanked BAC vector sequence.

Therefore, a preferred form of this embodiment relates to a recombinant Koi herpesvirus according to the invention, characterised in that part of the BAC vector sequence is excised from the herpesvirus genome thereby leaving a heterologous sequence at the excision site or former insertion site, respectively, in the herpesvirus genome.

And in a more preferred form of this embodiment, the part of the BAC vector sequence that is excised from the herpesvirus genome comprises at least one gene encoding a selectable marker and/or a resistance gene.

It is also possible to remove entirely the BAC cassette sequence by homologous recombination in eukaryotic cells using a DNA fragment of the wild type viral genome encompassing the site of insertion of the BAC cassette (e.g. ORF55 encoding TK). Selection of viral plaques that do not longer express EGFP (encoded by the BAC cassette) allows the selection of recombinants which have reverted the site of BAC insertion to wild type sequence.

The recombinant Koi herpesvirus according to the present invention in either form, the KHV BAC clone, and the above mentioned KHV construct where at least part of the BAC vector sequence is excised from the herpesvirus genome may be used for further manipulation involving for example genetic engineering techniques in order to make the genome deficient in further specific genes. The deficiency of such further genes can equally be obtained using the BAC technique, as already said above.

Although a recombinant KHV according to the invention can be used for vaccine purposes as such (see below), merely in order to prevent fish, more specifically carp, even more specifically *Cyprinus carpio carpio* or *Cyprinus carpio koi*, from KHV disease, it can also be efficiently used as carrier virus for heterologous (i.e. non-KHV) DNA fragment. In that case, the advantageous characteristics of the recombinant KHV according to the invention would be fully used and in addition the virus would e.g. gain additional properties such as marker properties, additional immunizing properties or adjuvating properties.

"Marker properties" in this respect means that the heterologous DNA fragment allows, directly or indirectly, to discriminate between field virus infection or vaccine virus infection. A direct way to discriminate between field virus infection and vaccine virus infection would e.g. comprise a PCR-reaction using primers that specifically reacts with a heterologous (i.e. non-KHV) DNA fragment in a recombinant KHV according to the invention, and not with DNA of a KHV field virus.

An indirect way to discriminate between field virus infection and vaccine virus infection would e.g. comprise an immunological reaction using an antibody that specifically reacts with an immunogenic protein encoded by a heterologous (i.e. non-KHV) DNA fragment in a recombinant KHV according to the invention, and not with any protein of a KHV field virus.

Thus, another embodiment of the present invention relates to a recombinant KHV according to the invention that comprises a heterologous DNA fragment, e.g. a heterologous gene.

Preferably, such a heterologous DNA fragment is a heterologous gene that encodes an immunogenic protein of another virus or microorganism that is pathogenic to fish, more specifically carp, even more specifically *Cyprinus carpio carpio* or *Cyprinus carpio koi*. More preferably, the heterologous gene is the G glycoprotein of rhabdovirus causing carp spring viraemia. Such a construct, when used in a vaccine, will not only protect carp against KHV but also against carp spring viraemia.

Suitable promoters for the expression of heterologous genes in eukaryotic cells are extensively known in the art. An example of a suitable promoter for the expression of a heterologous gene, e.g. the G glycoprotein of rhabdovirus causing carp spring viraemia is the HCMV IE promoter.

The present invention further provides a method for the production of infectious particles of recombinant Koi herpesvirus (KHV), wherein said method comprises the steps of:

(a) introducing a recombinant KHV according to the invention or a recombinant KHV DNA comprising the genome of a recombinant KHV according to the invention into permissive eukaryotic cells; and
(b) culturing the host cell to produce recombinant Koi herpesvirus (KHV)

Due to their attenuated character, the above mentioned recombinant Koi herpesviruses according to the invention and their DNA are very suitable for the immunization of fish, preferably *Cyprinus carpio carpio* or *Cyprinus carpio koi* individuals by injection or balneation or per os.

Therefore, still another embodiment of the present invention provides a recombinant Koi herpesvirus according to the invention and/or a KHV DNA comprising the genome of the recombinant Koi herpesvirus according to the invention for use in the prevention and/or therapeutic treatment of a disease in fish caused by Koi herpesvirus (KHV).

Preventive use is a use that aims at preventing infection, or at least clinical manifestations of the disease. Therapeutic use is a use of said KHV or KHV DNA in fish that already suffer from the disease caused by KHV.

Again another embodiment of the present invention provides a recombinant Koi herpesvirus according to the invention and/or a KHV DNA comprising the genome of the recombinant Koi herpesvirus according to the invention for use in a vaccine for the prevention and/or therapeutic treatment of a disease in fish caused by Koi herpesvirus (KHV).

Still another embodiment of the present invention provides a vaccine for the prevention and/or therapeutic treatment of a disease in fish caused by Koi herpesvirus (KHV), characterised in that said vaccine comprises a recombinant Koi herpesvirus according to the invention and/or a KHV DNA comprising the genome of the recombinant Koi herpesvirus according to the invention, and a pharmaceutically acceptable carrier.

Again another embodiment of the present invention provides a vaccine for prevention and/or therapeutic treatment of a disease in fish caused by a rhabdovirus causing carp spring viraemia, which vaccine comprises a recombinant KHV according to the invention carrying the gene encoding G glycoprotein of said rhabdovirus causing carp spring viraemia or a DNA sequence comprising the genome of said recombinant KHV, and a pharmaceutically acceptable carrier.

As used herein, the term "vaccine" refers to a composition capable of prevention and/or therapeutic treatment of a host to a particular disease. Such a vaccine may produce prophylactic or therapeutic immunity.

The pharmaceutically acceptable carrier can be as simple as water or a buffer. The pharmaceutically acceptable carrier may also comprise stabilizers. It can also comprise an adjuvant, or it can in itself be an adjuvant.

Typically, vaccines are prepared as liquid solutions, emulsions or suspensions for injection or delivery through immersion of fish in water. For instance, a liquid emulsion or emulsifiable concentrate can be prepared in order to be added to a water tank or bath where the fish are held. Solid (e.g. powder) forms suitable for dissolution in, or suspension in, liquid vehicles or for mixing with solid food, prior to administration may also be prepared. The vaccine may be a lyophilized culture in a ready to use form for reconstitution with a sterile diluent. For instance, lyophilized cells may be reconstituted in 0.9% saline (optionally provided as part of the packaged vaccine product). A preferred formulation of injectable vaccine is an emulsion. Liquid or reconstituted forms of the vaccine may be diluted in a small volume of water (e.g. 1 to 100 volumes) before addition to a pen, tank or bath.

In one preferred form of this embodiment, the vaccine preparation comprising the recombinant KHV strain is in a dry form, e. g. in a powder form, lyophilized, in a compressed pellet or tablet form, etc.

In another form of this embodiment, said virus may be in the form of a tissue culture fluid. Said fluid may be stored at the ambience, preferably at −70° C., most preferably as a solution containing glycerol. In one specific example, the tissue culture fluid contains 20% glycerol.

The recombinant KHV strain disclosed in the present invention may be converted into a dry form by a number of methods. A particularly preferred form of drying is through lyophilization. Prior to drying, e.g. lyophilization procedure, a variety of ingredients may be added to the medium such as preservatives, anti-oxidants or reducing agents, a variety of excipients, etc. Such excipients may also be added to the dry, e. g. lyophilized active-attenuated virus also after the drying step.

When the recombinant KHV according to the invention is used as a vaccine component for oral administration (e.g. through dipping or balneation), there will usually be no need for the administration of an adjuvant.

If however the vaccine preparation is injected directly into the fish, the use of an adjuvant is optional. If the recombinant KHV according to the invention is in a non-replicating form, the addition of immune stimulants may be preferred.

In general, in order to boost the immune response, the preparation may include a variety of adjuvants, cytokines or other immune stimulants, particularly in the case of preparations that are intended for injection.

An adjuvant is an immunostimulatory substance boosting the immune response of the host in a non-specific manner. The adjuvant may be hydrophilic adjuvant, e.g., aluminum hydroxide or aluminum phosphate, or hydrophobic adjuvant, e.g. mineral oil based adjuvants. Adjuvants such as muramyl dipeptides, avidine, aluminium hydroxide, aluminium phosphate, oils, oil emulsions, saponins, dextran sulphate, glucans, cytokines, block co-polymers, immunostimulatory oligonucleotides and others known in the art may be admixed with the recombinant KHV according to the invention. Examples of adjuvants frequently used in fish farming are muramyldipeptides, lipopolysaccharides, several glucans and glycans and Carbopol® (a homopolymer). Suitable adjuvants are e.g. water in oil (w/o) emulsions, o/w emulsions and w/o/w double-emulsions. Oil adjuvants suitable for use in w/o emulsions are e.g. mineral oils or metabolisable oils. Mineral oils are e.g. Bayol®, Marcol® and Drakeol®; metabolisable oils are e.g. vegetable oils, such as peanut oil and soybean oil, or animal oils such as the fish oils squalane and squalene. Alternatively a vitamin E (tocopherol) solubilisate as described in EP 382,271 may advantageously be used. Very suitable o/w emulsions are e.g. obtained starting from 5-50% w/w water phase and 95-50% w/w oil adjuvant, more preferably 20-50% w/w water phase and 80-50 w/w oil adjuvant are used. The amount of adjuvant added depends on the nature of the adjuvant itself, and information with respect to such amounts provided by the manufacturer.

In a preferred embodiment the vaccine according to the invention additionally comprises a stabilizer. A stabilizer can be added to a vaccine according to the invention e.g. to protect it from degradation, to enhance the shelf-life, or to improve freeze-drying efficiency. Useful stabilizers are i.a. SPGA (Bovarnik et al., 1950, J. Bacteriology, vol. 59, p. 509), skimmed milk, gelatine, bovine serum albumin, carbohydrates e.g. sorbitol, mannitol, trehalose, starch, sucrose, dextran or glucose, lactoses, proteins such as albumin or casein or degradation products thereof, and buffers, such as alkali metal phosphates.

Antibiotics such as neomycin and streptomycin may be added to prevent the potential growth of germs.

In addition, the vaccine may comprise one or more suitable surface-active compounds or emulsifiers, e.g. Span® or Tween®. The vaccine may also comprise a so-called "vehicle". A vehicle is a compound to which the KHV virus (either in form of a virus particle or in form of DNA) according to the invention adheres, without being covalently bound to it. Such vehicles are i.a. bio-microcapsules, micro-alginates, liposomes and macrosols, all known in the art. A special form of such a vehicle is an Iscom. It goes without saying that admixing other stabilizers, carriers, diluents, emulsions, and the like to vaccines according to the invention are also within the scope of the invention. Such additives are for instance described in well-known handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN: 0444819681).

The recombinant KHV when used in its dry form in a vaccine may further include a reconstitution fluid, preferably sterile water, saline or physiological solution. It may also contain small amounts of residual materials from the manufacturing process such as cell proteins, DNA, RNA, etc. While these materials are not additives per se, they may nonetheless be present in the vaccine formulation.

The vaccine may be administered to fish individually-orally, e.g. through their feed or by forced oral administration, or by injection (e.g. via the intramuscular or intraperitoneal route).

Alternatively the vaccine may be administered simultaneously to the entire fish population contained in a body of water by spraying, dissolving and/or immersing the vaccine. These methods are useful for vaccination of all kinds of fish, e.g., food and ornamental fish, and in various environments such as ponds, aquariums, natural habitat and fresh water reservoirs.

A further aspect of the invention relates to a DNA vaccine comprising the recombinant KHV according to the invention.

DNA vaccines according to the invention do not basically differ from vaccines comprising the recombinant KHV according to the invention, in the sense that they comprise the genome of a recombinant KHV according to the invention. They can easily be administered through intradermal application e.g. using a needle-less injector such as a Gene-Gun®. This way of administration delivers the DNA directly into the cells of the animal to be vaccinated. A preferred amount of a recombinant KHV DNA according to the invention, in a pharmaceutical composition according to the invention (as outlined below) is in the range between 10 pg and 1000 μg. Preferably, amounts in the range between 0.1 and 100 μg are used. Alternatively, fish can be immersed in solutions comprising e.g. between 10 pg and 1000 μg/ml of the DNA to be administered. All these techniques and routes of administration are well-known in the art.

Preferably the vaccine according to the invention is formulated in a form suitable for injection or for immersion vaccination, such as a suspension, solution, dispersion, emulsion, and the like.

The dosing scheme for the application of a vaccine according to the invention to the target organism can be the application of single or multiple doses, which may be given at the same time or sequentially, in a manner compatible with the dosage and formulation and in such an amount as will be immunologically effective. It is well within the capacity of the skilled person to determine whether a treatment is "immunologically effective", for instance by administering an experimental challenge infection to vaccinated animals, and next determining a target animals' clinical signs of disease, serological parameters, or by measuring re-isolation of the pathogen. What constitutes a "pharmaceutically effective amount" for a vaccine according to the invention that is based upon a recombinant KHV or a recombinant KHV DNA according to the invention, is dependent on the desired effect and on the target organism. Determination of the effective amount is well within the skills of the routine practitioner. A preferred amount of a recombinant KHV DNA according to the invention, comprised in a pharmaceutical composition according to the invention, has been described above.

A preferred amount of a live vaccine comprising recombinant KHV virus strain according to the invention is expressed for instance as plaque forming units (pfu). For instance for a live viral vector a dose range between 1 and $10^{10}$ plaque forming units (pfu) per animal dose may advantageously be used; preferably a range between $10^2$ and $10^6$ pfu/dose.

Many ways of administration can be applied, all known in the art. The vaccines according to the invention are preferably administered to the fish via injection (intramuscular or the intraperitoneal route), immersion, dipping or per os. The protocol for the administration can be optimized in accordance with standard vaccination practice.

If a vaccine comprises a non-replicative form of the recombinant KHV according to the invention, the dose would be expressed as the number of non-replicative virus particles to be administered. Then dose would usually be somewhat higher when compared to the administration of live virus particles, because live virus particles replicate to a certain extent in the target animal, before they are removed by the immune system. For vaccines on the basis of non-replicative virus particles, an amount of virus particles in the range of about $10^4$ to $10^9$ particles would usually be suitable.

Preferably the vaccine is administered via immersion, especially when a live recombinant KHV according to the invention is used. This is especially efficient in case of the use of such vaccines in the setting of commercial aquaculture farming.

LEGEND TO THE FIGURES

FIG. 1: schematic representation of the CyHV-3 genome region encompassing ORF57. The coordinates of ATG and stop codons of each ORF (according to Genbank accession N° NC_009127) are indicated. The coordinates of putative promoters (P) identified by in silico analyses within or close to ORF56 and ORF57 are presented. The number following the letter P identifies the ORF under control of the identified promoter sequence. Selected sequences to be deleted in order to invalidate ORF56 and/or ORF57 are represented at the top. The coordinates of the deletions are indicated.

Figure 2:
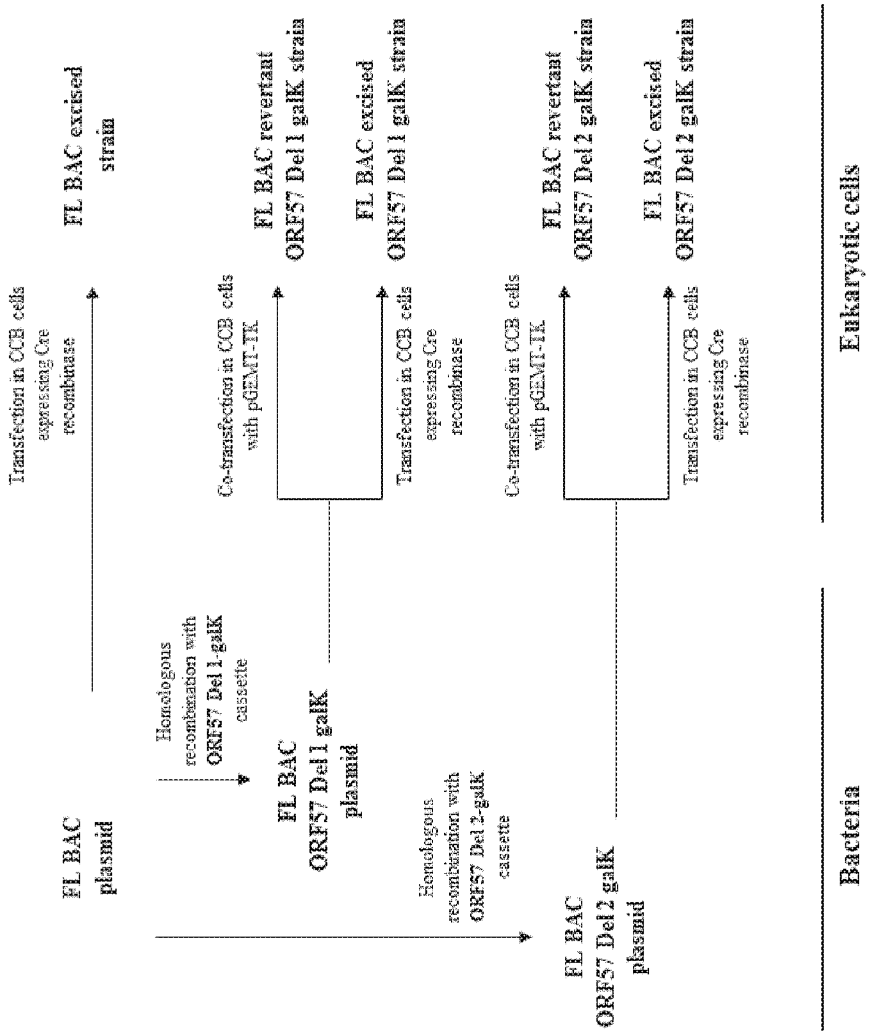
Figure 3:
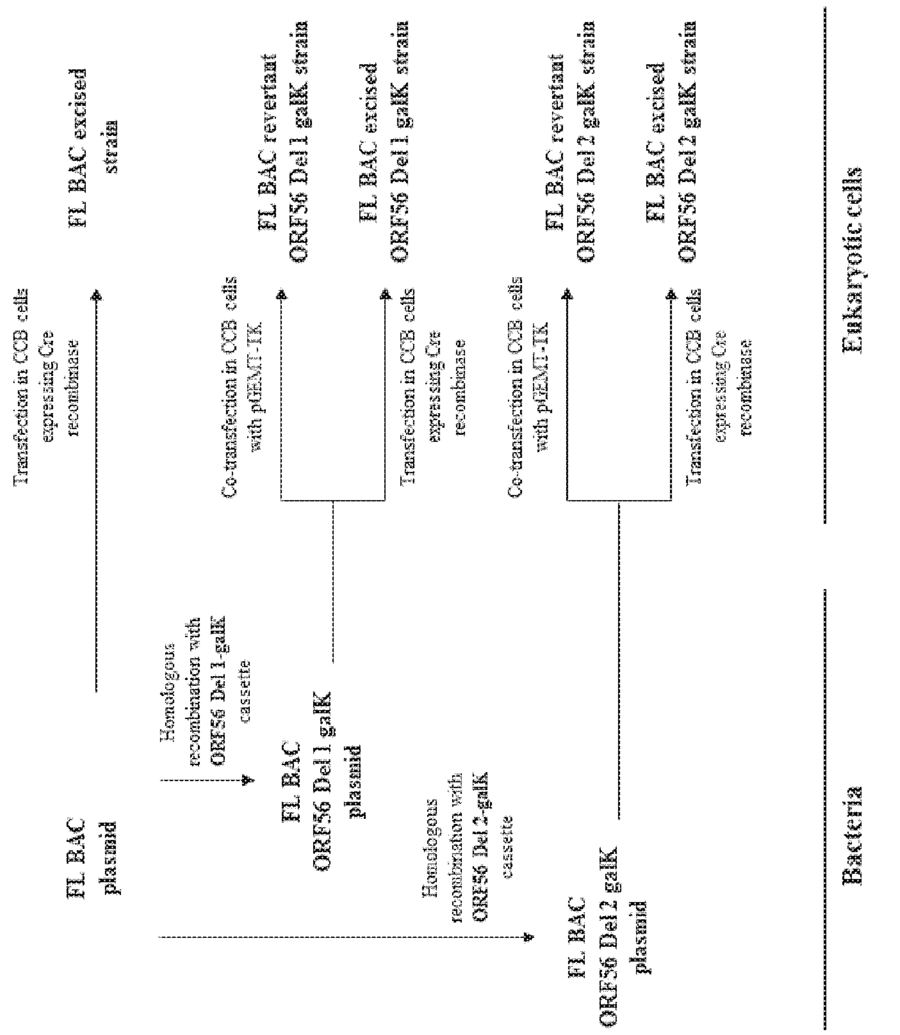

FIGS. 2 and 3: flowchart of stages performed to produce FL BAC galK recombinant plasmids deleted for ORF57 (FIG. 2) or ORF56 (FIG. 3), and to demonstrate the reconstitution of infectious virus from the produced plasmids. The regions of ORF57 or ORF56, as identified in FIG. 1, were replaced by a galK expression cassette using homologous recombination in *E. coli*. To reconstitute infectious virus with a wild type thymidine kinase (TK) locus (FL BAC revertant strains), the recombinant plasmids were co-transfected in permissive CCB cells with pGEMT-TK plasmid. To reconstitute infectious virus with a truncated form of TK (FL BAC excised strains), the recombinant plasmids were transfected in CCB cells expressing Cre recombinase.

Figure 4:
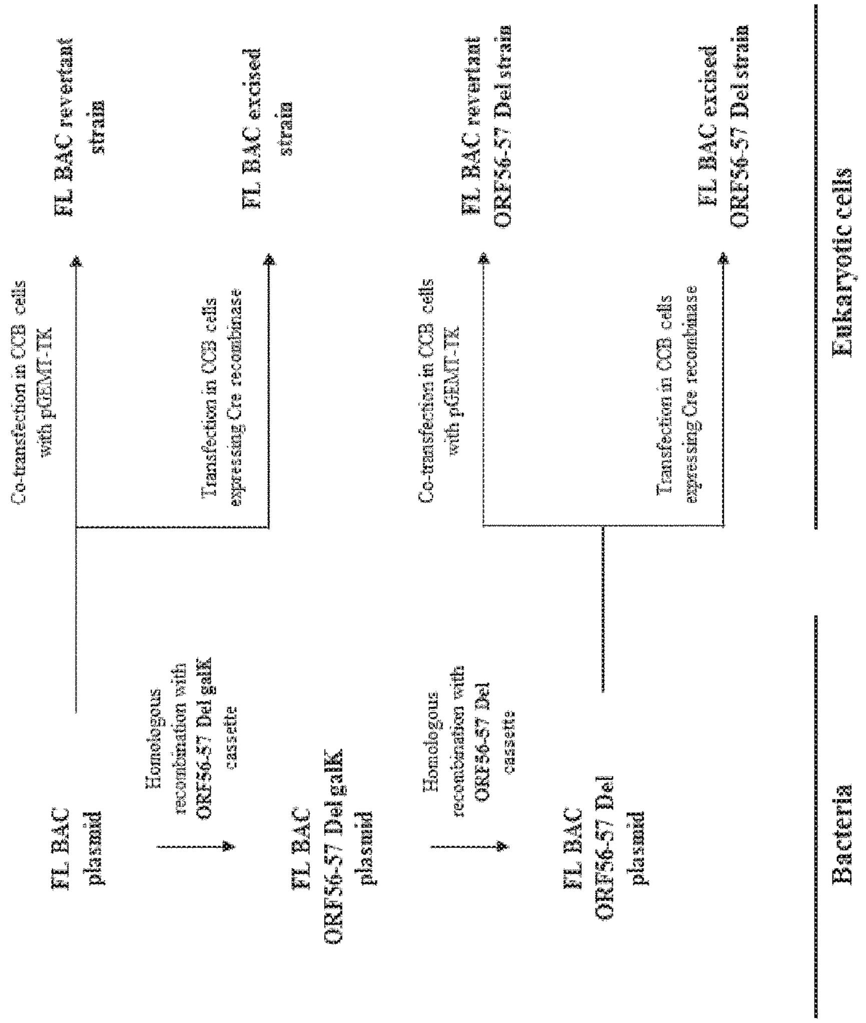

FIG. 4: flowchart of stages performed to produce FL BAC recombinant plasmids deleted for ORF57 and ORF56 (ORF56-57), and to demonstrate the reconstitution of infectious virus from the produced plasmids. The region of ORF56-57, as identified in FIG. 1, was replaced by a galK expression cassette using homologous recombination in *E. coli*. The galK expression cassette was then removed by homologous recombination with a synthetic DNA sequence corresponding to KHV genome regions flanking the galK expression cassette (ORF56-57 Del cassette). To reconstitute infectious virus with a wild type thymidine kinase (TK) locus (FL BAC revertant strains), the recombinant plasmid was co-transfected in permissive CCB cells with pGEMT-TK plasmid. To reconstitute infectious virus with a truncated form of TK (FL BAC excised strains), the recombinant plasmid was transfected in CCB cells expressing Cre recombinase.

FIGS. 5A-5G: safety (Figures A-D) and vaccination/challenge (FIGS. E-G) tests of ORF57 single deleted recombinants. The safety of the FL BAC excised ORF57 Del 1 galK (FIG. A) and the FL BAC excised ORF57 Del 2 galK (FIG. B) strains was tested as described in the examples (Safety tests) on common carp (7 months old, mean weight of 3.74 g, n=20). The FL BAC excised strain (FIG. C) and mock-infection (FIG. D) were used as positive and negative controls, respectively. Percentages of surviving carp are expressed according to days post-infection taking day 0 as the reference. Six weeks post-infection with the ORF57 single deleted recombinants (Figures E and F), fish were challenged as described in the examples (vaccination/challenge). Mock-infected fish were used as controls (FIG. G). Percentages of surviving carp are expressed according to days post-infection taking day 42 as the reference.

FIGS. 6A-6D: safety of ORF56 single deleted recombinants.

The safety of the FL BAC excised ORF56 Del 1 galK (FIG. A) and the FL BAC excised ORF56 Del 2 galK (FIG. B) strains was tested as described in the examples (Safety tests) on common carp (7 months old, mean weight of 3.74 g, n=20). The FL BAC excised strain (FIG. C) and mock-infection (FIG. D) were used as positive and negative controls, respectively. Percentages of surviving carp are expressed according to days post-infection taking day 0 as the reference.

FIGS. 7A-7G: safety (Figures A-C) and vaccination/challenge (Figures D-G) tests of the FL BAC excised ORF56-57 Del strain. The safety of the FL BAC excised ORF56-57 Del strain (FIG. B) was tested as described in the examples (Safety tests) on common carp (7 months old, mean weight of 4.41 g, n=30). The FL BAC excised strain (FIG. A) and mock-infection (FIG. C) were used as positive and negative controls, respectively. Mock-infection was performed on duplicate groups. Percentages of surviving carp are expressed according to days post-infection taking day 0 as the reference. Vaccination/challenge (FIGS. D-G) tests. Fish (n=15) vaccinated with the FL BAC excised ORF56-57 Del strain were challenged with the KHV FL strain at 3 weeks (FIG. D) or 6 weeks (FIG. F) post-vaccination as described in the examples (vaccination/challenge). Duplicate groups of mock-infected fish were used as controls (FIGS. E and G). Percentages of surviving carp are expressed according to days post-infection taking the day of the challenge as the reference.

FIGS. 8A-8G: safety (FIGS. A-C) and vaccination/challenge (FIGS. D-G) tests of the FL BAC revertant ORF56-57 Del strain. The safety of the FL BAC revertant ORF56-57 Del strain (FIG. B) was tested as described in the examples (Safety tests) on common carp (7 months old, mean weight of 3.74 g, n=30). The FL BAC revertant strain (FIG. A) and mock-infection (FIG. C) were used as positive and negative controls, respectively. Mock-infection was performed on duplicate groups. Percentages of surviving carp are expressed according to days post-infection taking day 0 as the reference. Vaccination/challenge (FIGS. D-G) tests. Fish (n=15) vaccinated with the FL BAC revertant ORF56-57 Del strain were challenged with the KHV FL strain at 3 weeks (FIG. D) or 6 weeks (FIG. F) post-vaccination as described in the examples (vaccination/challenge). Duplicate groups of mock-infected fish were used as controls (FIGS. E and G). Percentages of surviving carp are expressed according to days post-infection taking the day of the challenge as the reference.

EXAMPLES a) Cells and Viruses

*Cyprinus carpio* brain cells (CCB) (Neukirch et al., 1999) were cultured in minimum essential medium (MEM, Invitrogen) containing 4.5 g/l glucose (D-glucose monohydrate, Merck) and 10% fetal calf serum (FCS). Cells were cultured at 25° C. in a humid atmosphere containing 5% $CO_2$. The CyHV-3 FL strain was isolated from the kidney of a fish which died from KHV (CER Marloie, Belgium).

b) CyHV-3 BAC Plasmid

The CyHV-3 FL BAC plasmid was used as parental plasmid to produce CyHV-3 recombinants. This plasmid has been extensively described in Costes et al (2008) and in International Patent Application WO 2009/027412. The CyHV-3 FL BAC plasmid is an infectious bacterial artificial chromosome (BAC) clone of the CyHV-3 FL strain genome. In this plasmid, the loxP-flanked BAC cassette is inserted into the CyHV-3 TK locus (ORF55).

c) Production of ORF 57 CyHV-3 FL BAC Recombinant Plasmids Using galK Positive Selection in Bacteria Two CyHV-3 FL BAC recombinant plasmids with deletion in the ORF57 locus (see ORF57 Del 1 and ORF57 Del 2 in FIG. 1) were produced using a galK positive selection in bacteria as previously described (Warming et al., 2005) (FIG. 2). The recombination fragment consisted of a galactokinase (galK) gene (1231 bp) flanked by 50 bp sequences homologous to the regions of the CyHV-3 genome flanking the sequence to be deleted (FIG. 1).

These fragments were produced by PCR using the pgalK vector as template. The following primers were used for the amplification (see Table 1 for primer sequence): for production of the ORF57 Del 1 deletion: primers ORF57 Del1 fwd and ORF57 Del1 rev leading to the ORF57 Del 1-galK amplicon; for production of the ORF57 Del 2 deletion: primers ORF57 Del2 fwd and ORF57 Del2 rev leading to the ORF57 Del 2-galK amplicon. The amplification product was purified (QIAquick Gel Extraction Kit). Next, electrocompetent SW102 cells containing the CyHV-3 FL BAC plasmid were electroporated with 50 ng of the PCR products described above. Electroporated cells were plated on solid M63 minimal medium supplemented with 20% galactose and chloramphenicol (17 μg/ml) to select bacteria in which homologous recombination occurred. Finally, colonies obtained were streaked onto MacConkey indicator plates as described elsewhere to confirm the production of galK positive clones. Recombinant BAC molecules were amplified and purified (QIAGEN Large-Construct Kit), and their molecular structure was controlled using a combined restriction endonuclease-Southern blot approach, PCR and sequencing.

TABLE 1

Oligonucleotides used for PCR amplification

| Primer | Sequence* | bp | Coordinates of underlined sequence according to Genbank accession No. NC_009127 |
|---|---|---|---|
| ORF57 Del1 fw | 5'-CGTACAGGGTGGCGGTGCACCTGTCCC<br>AGAAGGCCTTCACCGCCTGG***GAGCTC***CCT<br>GTTGACAATTAATCATCGGCA-3' | 77 bp | 99551-99599 |
| ORF57 Del1 rev | 5'-CGGCTCATCATCTGCGGGTCCATCCAG<br>GCGCCCTTGCCCCACAGCAGAGC**T**TCAGC<br>ACTGTCCTGCTCCTT-3' | 71 bp | 99743-99694 |
| ORF57 Del2 fw | 5'-CTTTGTGCTGCACAAGGGCTTCAACCAC<br>CACTACGCCTTCTGCGATCACCCCTGTTGA<br>CAATTAATCATCGGCA-3' | 74 bp | 99894-99943 |
| ORF57 Del2 rev | 5'-CTGAGCGTTGTTGAAGGCCTCCATCAGG<br>TGCTGCCTGATCTGCTTGTGCA***GAGCTC***<br>GCACTGTCCTGCTCCTT-3' | 74 bp | 100161-100112 |

*The primers represent sequences homologous to CyHV-3 genome (underlined sequences) and to galK expression cassette.

d) Reconstitution of Infectious Virus from ORF 57 CyHV-3 FL BAC Recombinant Plasmid CyHV-3 BAC plasmids were transfected (Lipofectamine Plus, Invitrogen) into permissive CCB. To produce BAC plasmid derived strains with a wild type TK locus, CyHV-3 BAC plasmids were co-transfected in CCB cells together with the pGEMT-TK vector (molecular ratio 1:75). Seven days post-transfection, viral plaques negative for EGFP expression (the BAC cassette encodes an EGFP expression cassette) were picked and enriched by three successive rounds of plaque purification. Similarly, to reconstitute virions with excised BAC cassette from the viral genome, BAC plasmids were co-transfected in CCB cells together with the pEFIN3-NLS-Cre vector encoding Cre recombinase fused to a nuclear localization signal (Costes et al; 2008 JVI) (molecular ratio: 1:70).

e) Production of ORF 56 CyHV-3 FL BAC Recombinant Plasmids Using galK Positive Selection in Bacteria Two CyHV-3 FL BAC recombinant plasmids with deletion in the ORF56 locus (see ORF56 Del 1 and ORF56 Del 2 in FIG. 1) were produced using a galK positive selection in bacteria as previously described (Warming et al., 2005) (FIG. 3). The recombination fragment consisted of a galactokinase (galK) gene (1231 bp) flanked by 50 bp sequences homologous to the regions of the CyHV-3 genome flanking the sequence to be deleted (FIG. 1). These fragments were produced by PCR using the pgalK vector as template. The following primers were used for the amplification (see Table 2 for primer sequence): for production of the ORF56 Del 1 deletion: primers ORF56 Del1 fwd and ORF56 Del1 rev leading to the ORF56 Del 1-galK amplicon; for production of the ORF56 Del 2 deletion: primers ORF56 Del2 fwd and ORF56 Del2 rev leading to the ORF56 Del 2-galK amplicon. The amplification product was purified (QIAquick Gel Extraction Kit). Next, electrocompetent SW102 cells containing the CyHV-3 FL BAC plasmid were electroporated with 50 ng of the PCR products described above. Electroporated cells were plated on solid M63 minimal medium supplemented with 20% galactose and chloramphenicol (17 μg/ml) to select bacteria in which homologous recombination occurred. Finally, colonies obtained were streaked onto MacConkey indicator plates as described elsewhere to confirm the production of galK positive clones. Recombinant BAC molecules were amplified and purified (QIAGEN Large-Construct Kit), and their molecular structure was controlled using a combined restriction endonuclease-Southern blot approach, PCR and sequencing.

TABLE 2

Oligonucleotides used for PCR amplification

| Primer | Sequence* | bp | Coordinates of underlined sequence according to Genbank accession No. NC_009127 |
|---|---|---|---|
| ORF56 Del1 fwd | 5'-TCAGGATCGAGGTCACCAGCTTGAGCTT<br>CTCGGGCATGTACTCGCGCCACCCTGTTG<br>ACAATTAATCATCGGCA-3' | 74 bp | 97475-97524 |
| ORF56 Del1 rev | 5'-CGGCGAGGTGATTTCGGTCATGAGCAA<br>ATCGATTGCGGCCGAACAGCAGCTCAGCA<br>CTGTCCTGCTCCTT-3' | 70 bp | 98361-98312 |

TABLE 2-continued

Oligonucleotides used for PCR amplification

| Primer | Sequence* | bp | Coordinates of underlined sequence according to Genbank accession No. NC_009127 |
|---|---|---|---|
| ORF56 Del2 fwd | 5'-GATCGGGTACGTCGGCGTGCGCCACTTGACCTTCCTCAACGTCCCCGTCACCTGTTGACAATTAATCATCGGCA-3' | 74 bp | 97275-97324 |
| ORF56 Del2 rev | 5'-GCGCACACCATCACCATCTGTCCCATGTCTCCCCAACGCTACACCGTGACTCAGCACTGTCCTGCTCCTT-3' | 70 bp | 98561-98512 |

*The primers represent sequences homologous to CyHV-3 genome (underlined sequences) and to galK expression cassette.

f) Reconstitution of Infectious Virus from ORF 56 CyHV-3 FL BAC Recombinant Plasmid CyHV-3 BAC plasmids were transfected (Lipofectamine Plus, Invitrogen) into permissive CCB. To produce BAC plasmid derived strains with a wild type TK locus, CyHV-3 BAC plasmids were co-transfected in CCB cells together with the pGEMT-TK vector (molecular ratio 1:75). Seven days post-transfection, viral plaques negative for EGFP expression (the BAC cassette encodes an EGFP expression cassette) were picked and enriched by three successive rounds of plaque purification. Similarly, to reconstitute virions with excised BAC cassette from the viral genome, BAC plasmids were co-transfected in CCB cells together with the pEFIN3-NLS-Cre vector encoding Cre recombinase fused to a nuclear localization signal (Costes et al; 2008 JVI) (molecular ratio: 1:70).

g) Production of ORF56-57 CyHV-3 FL BAC Recombinant Plasmids Using galK Positive and Negative Selections in Bacteria CyHV-3 FL BAC recombinant plasmids with deletion in the ORF56 and ORF57 loci (FIG. 1) were produced using galK positive and negative selections in bacteria as previously described (Warming et al., 2005) (FIG. 4). The first recombination process (galK positive selection) was to replace the identified sequence of ORF56 and ORF57 by the galactokinase (galK) gene (1231 bp). The recombination fragment consisted of the galK gene flanked by 50 bp sequences homologous to the regions of the CyHV-3 genome flanking the sequence to be deleted (FIG. 1) (ORF56-57 Del galK, FIG. 4). This fragment was produced by PCR using the primers ORF56-ORF57 Del fw and ORF56-ORF57 Del rev (Table 3) and the pgalK vector as template. The amplification product was purified (QIAquick Gel Extraction Kit). Next, electrocompetent SW102 cells containing the CyHV-3 FL BAC plasmid were electroporated with 50 ng of the PCR product described above. Electroporated cells were plated on solid M63 minimal medium supplemented with 20% galactose and chloramphenicol (17 μg/ml) to select bacteria in which homologous recombination occurred. Finally, colonies obtained were streaked onto MacConkey indicator plates as described elsewhere to confirm the production of galK positive clones. Recombinant BAC molecules were amplified and purified (QIAGEN Large-Construct Kit), and their molecular structure was controlled using a combined restriction endonuclease-Southern blot approach, PCR and sequencing. The second recombination process (galK negative selection) was to remove the galK cassette from the FL BAC ORF56-57 Del galK plasmid. A synthetic 499 bp DNA fragment (ORF56-57 Del cassette, vide infra) was used to reach this goal. It consists of sequences homologous to the regions of the CyHV-3 genome flanking the sequence to be deleted: 250 bp (from coordinates 96751 to 9700, Genbank accession N° NC_009127) upstream of the galK gene and 249 bp (from coordinates 99751 to 100000 with deletion of base 99760, Genbank accession N° NC_009127) downstream on the galKgene. Electrocompetent SW102 cells containing the FL BAC ORF56-57 Del galK plasmid were electroporated with 50 ng of the PCR product described above. Electroporated cells were plated on solid minimal medium supplemented with 2-deoxy-galactose to select bacteria in which homologous recombination occurred (digestion of 2-deoxy-galactose by galK produce toxic products). Recombinant BAC molecules were amplified and purified (QIAGEN Large-Construct Kit), and their molecular structure was controlled using a combined restriction endonuclease-Southern blot approach, PCR and sequencing.

ORF56-57 Del Cassette:

```
5'-
tttgtcaaccagtcctccagggtcggtttggcgctggcctccttgccctt
ggtcacggcgatggcagacgccacaatcctcgcgacgggttccgtcagag
cagagttcttaaacatttcgacgcctcctccgacggtgaaccactctgac
caattcaggtcggagggccacgtctgcctgtgcatcatcgtctgcacagc
gtccctcgacagccccagcccgcacagcagtcgccactcttccctgttga
gtgcacgactcgtcaagatcaagctgcttgagcgcgtcgtgtacgggttc
atgatggccctgcagaaggcgctgcgcattcagaagcagggctgcaggat
ggtggggctcgaggacccggagaaggtggaggatatgaagaactttgtgc
tgcacaagggcttcaaccaccactacgccttctgcgatcaccactggcag
cactgggccctgggccgctccttcgagggcgagctgcccgacgtggtgg-
3'
```

TABLE 3

| Primer | Sequence* | bp | Coordinates of underlined sequence according to Genbank accession No. NC_009127 |
|---|---|---|---|
| ORF56-ORF57 Del fwd | 5'-GTCCCTCGACAGCCCCAGCCCGCACAGCAGTCGCCACTCTTCCCTGTTGATCAGCACTGTCCTGCTCCTT-3' | 70 bp | 96951-97000 |
| ORF56-ORF57 Del rev | 5'-AACCCGTACACGACGCGCTCAAGCAGCTTGATCTTGACGACGTCGTGCACCCTGTTGACAATTAATCATCGGCA-3' | 74 bp | 99800-99751 |

Oligonucleotides used for PCR amplification

*The primers represent sequences homologous to CyHV-3 genome (underlined sequences) and to galK expression cassette.

h) Reconstitution of Infectious Virus from ORF56-57 CyHV-3 FL BAC Recombinant Plasmid CyHV-3 BAC plasmids were transfected (Lipofectamine Plus, Invitrogen) into permissive CCB. To produce BAC plasmid derived strains with a wild type TK locus, CyHV-3 BAC plasmids were co-transfected in CCB cells together with the pGEMT-TK vector (molecular ratio 1:75). Seven days post-transfection, viral plaques negative for EGFP expression (the BAC cassette encodes an EGFP expression cassette) were picked and enriched by three successive rounds of plaque purification. Similarly, to reconstitute virions with excised BAC cassette from the viral genome, BAC plasmids were co-transfected in CCB cells together with the pEFIN3-NLS-Cre vector encoding Cre recombinase fused to a nuclear localization signal (Costes et al; 2008 JVI) (molecular ratio: 1:70).

i) Safety Tests

Common carp were acclimatized in 60-liter tanks at 24° C. for 10 days. Carp (biomass of 50 g of fish/l) were immersed for 2 h in water containing 4, 40 or 400 PFU/ml of the KHV strain to be tested. The control group (mock-infected) was immersed in water in which an equal volume of culture medium has been added. At the end of the incubation period, the fish were returned to the larger tank. The viral inoculums were titrated before inoculation and back-titrated after inoculation to ensure that the doses were equivalent between groups. Fishes were examined daily for clinical signs of KHV disease and dead fishes were removed.

j) Vaccination/Challenge

Common carp were acclimatized in 60-liter tanks at 24° C. for 10 days. For vaccination, carp (biomass of 50 g of fish/l) were immersed for 2 h in water containing 4, 40 or 400 PFU/ml of the KHV strain to be tested. At the end of the incubation period, the fish were returned to the larger tank. At 3 weeks or 6 weeks post-vaccination, fish were challenged with virulent KHV by co-habitation with naïve fish infected just before their release in the tank of vaccinated fish. These fish were inoculated by immersion in water containing 300 PFU/ml of the virulent parental FL strain for 2 h. Two infected fish were added to each tank containing vaccinated fish.

k) Safety and Challenge Results

The safety of the FL BAC excised ORF57 Del 1 galK (FIG. 5A) and the FL BAC excised ORF57 Del 2 galK (FIG. 5B) strains was tested as described in the examples (Safety tests) on common carp (7 months old, mean weight of 3.74 g, n=20). The FL BAC excised strain (FIG. 5C) and mock-infection (FIG. 5D) were used as positive and negative controls, respectively. Percentages of surviving carp were expressed according to day's post-infection taking day 0 as the reference. Six weeks post-infection with the ORF57 single deleted recombinants (FIGS. 5E and F), fish were challenged as described in the examples (vaccination/challenge). Mock-infected fish were used as controls (FIG. 5G). Percentages of surviving carp are expressed according to day's post-infection taking day 42 as the reference.

Figure 5A:
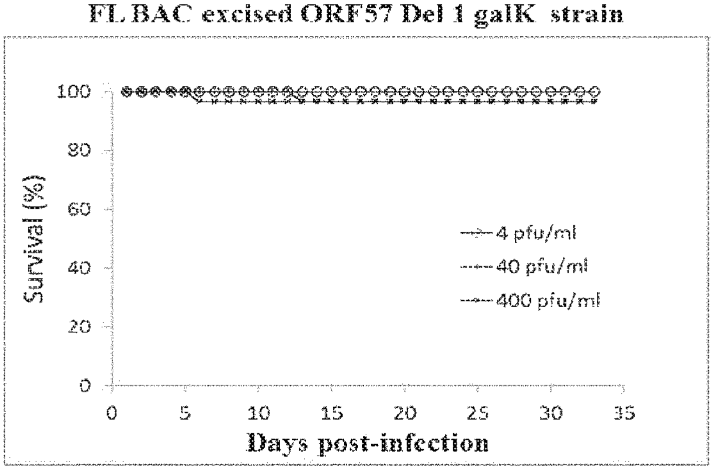
Figure 5B:
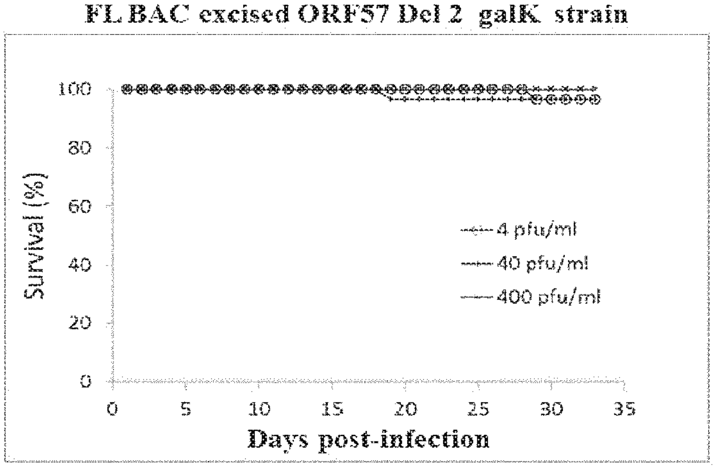
Figure 5C:
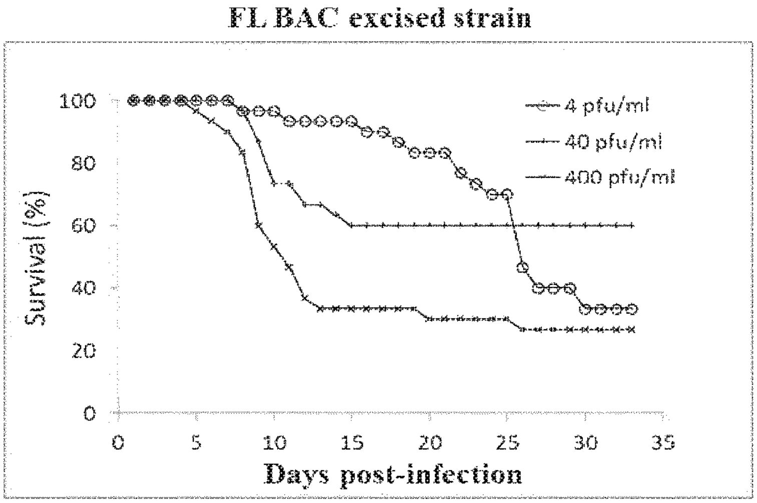
Figure 5D:
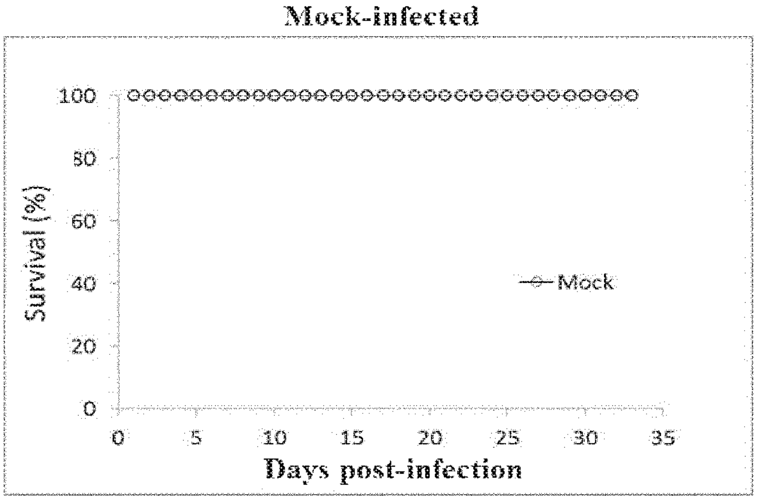

It is clear from FIGS. 5A and B that an ORF57 deletion mutant according to the invention is safe, even when applied to small fish.

Figure 5E:
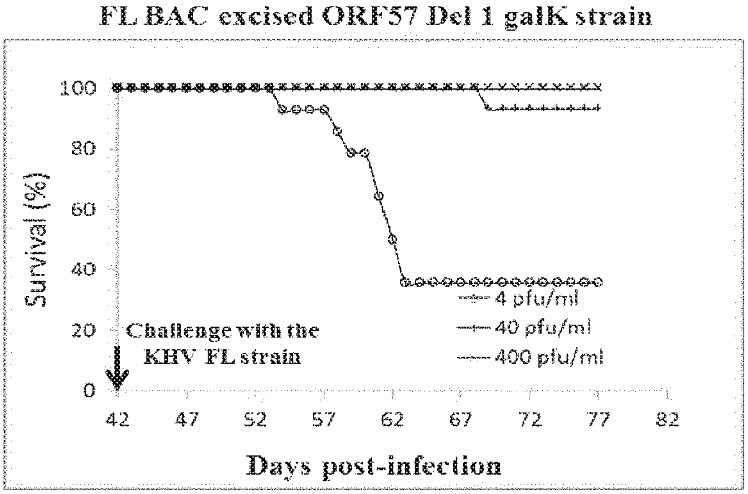
Figure 5F:
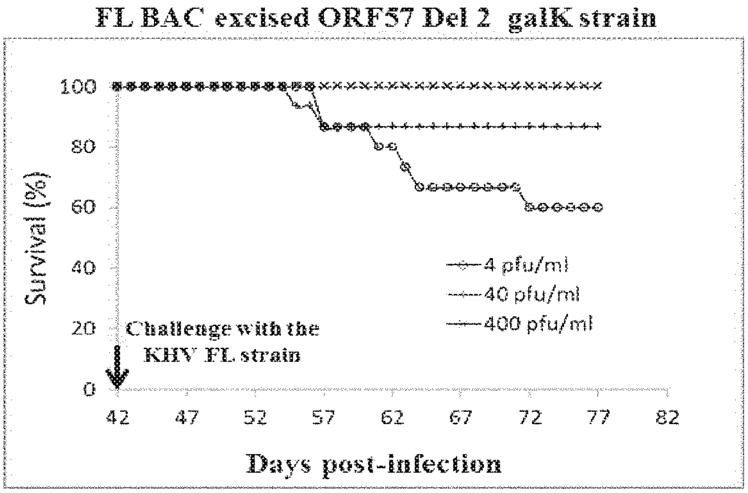
Figure 5G:
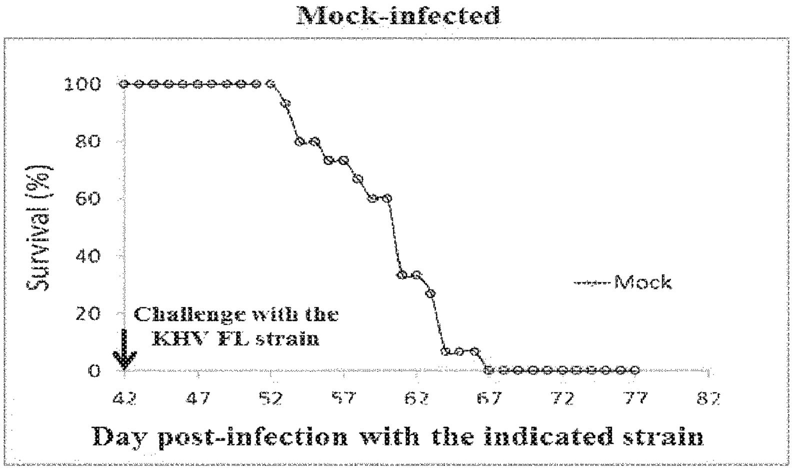
Figure 6A:
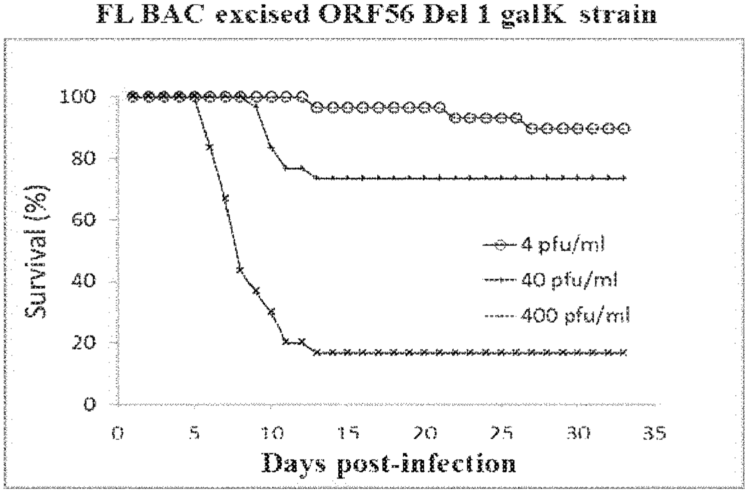
Figure 6B:
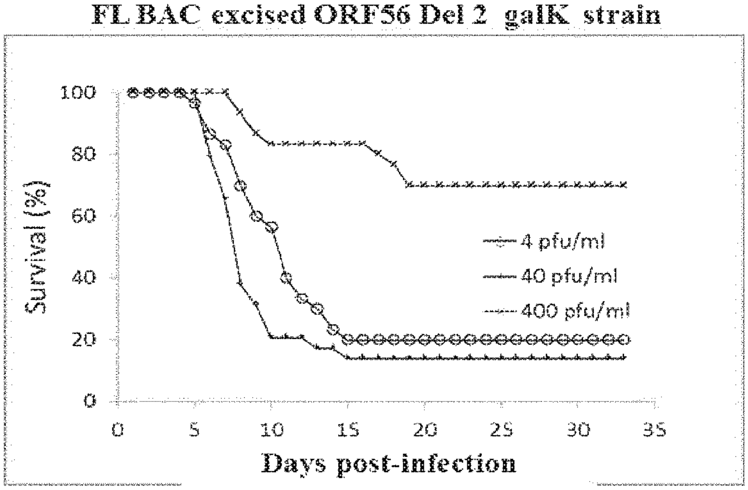
Figure 6C:
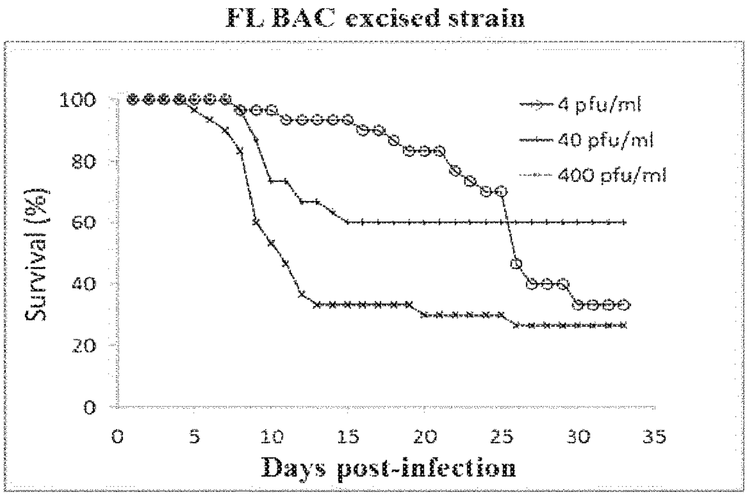
Figure 6D:
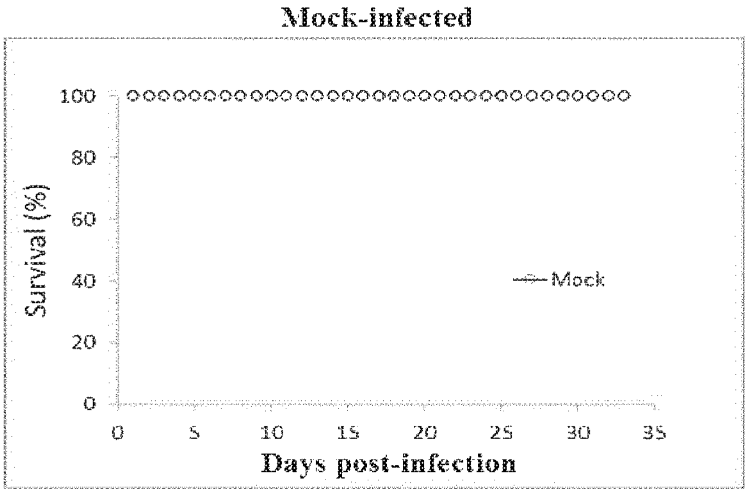
Figure 7A:
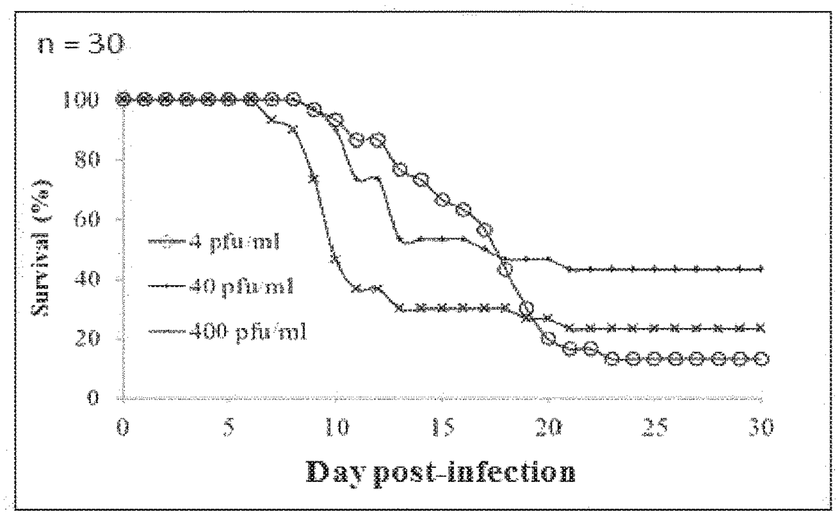
Figure 7B:
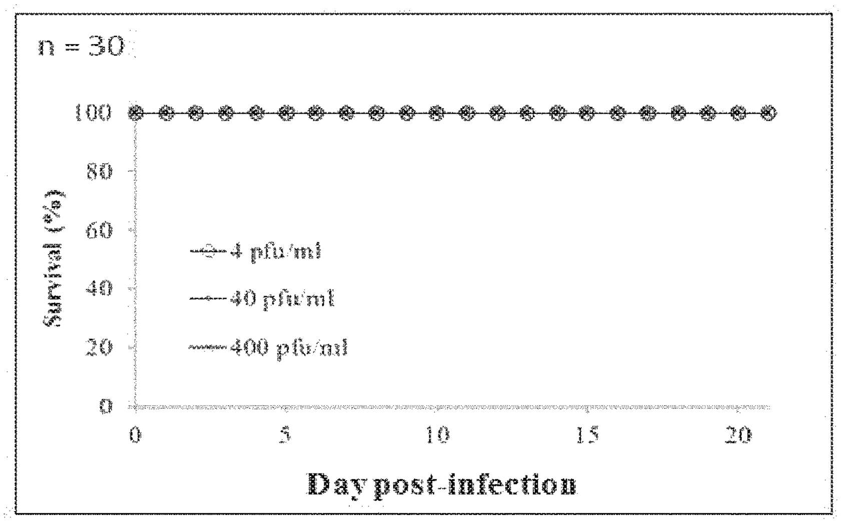
Figure 7C:
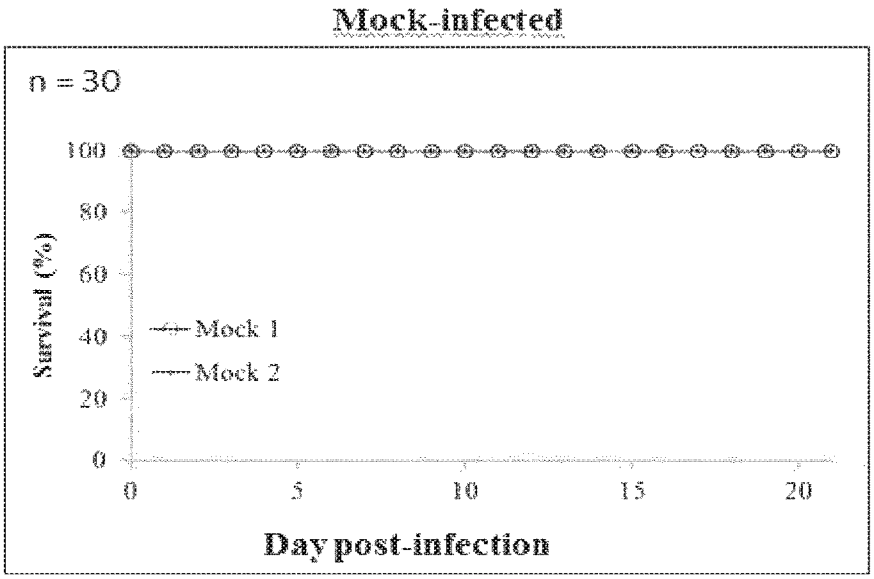
Figure 7D:
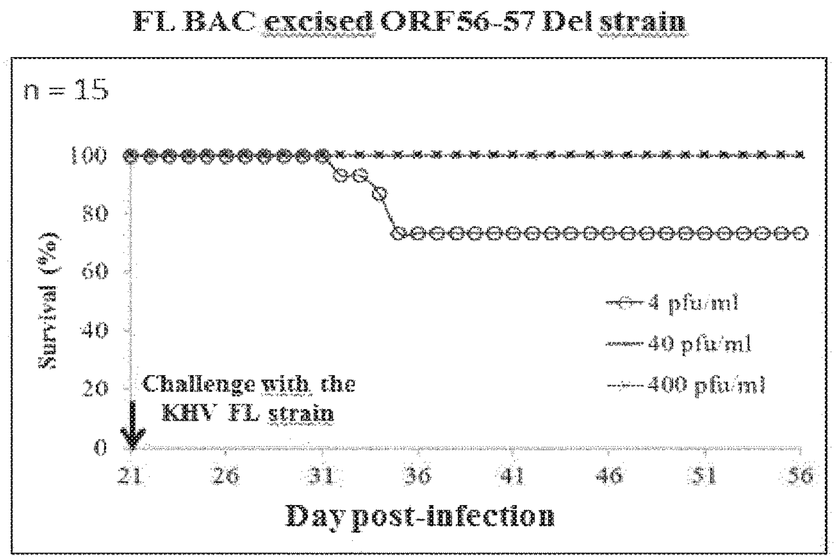
Figure 7E:
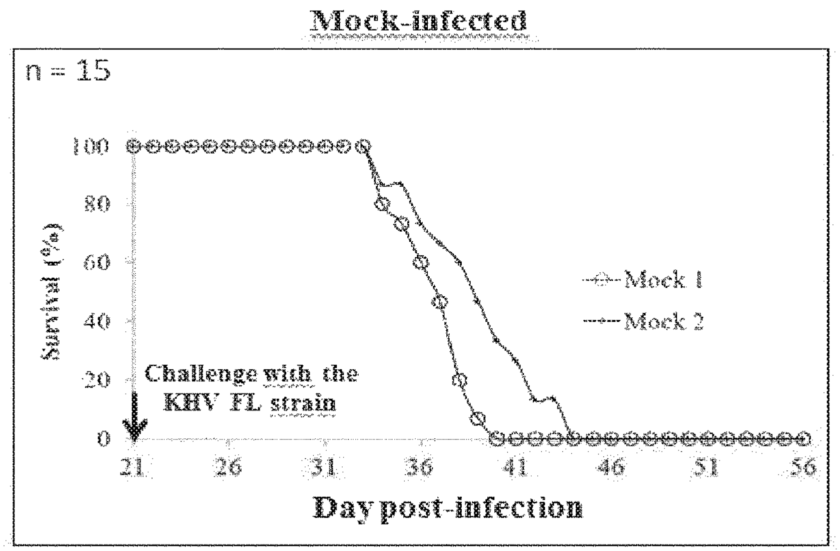
Figure 7F:
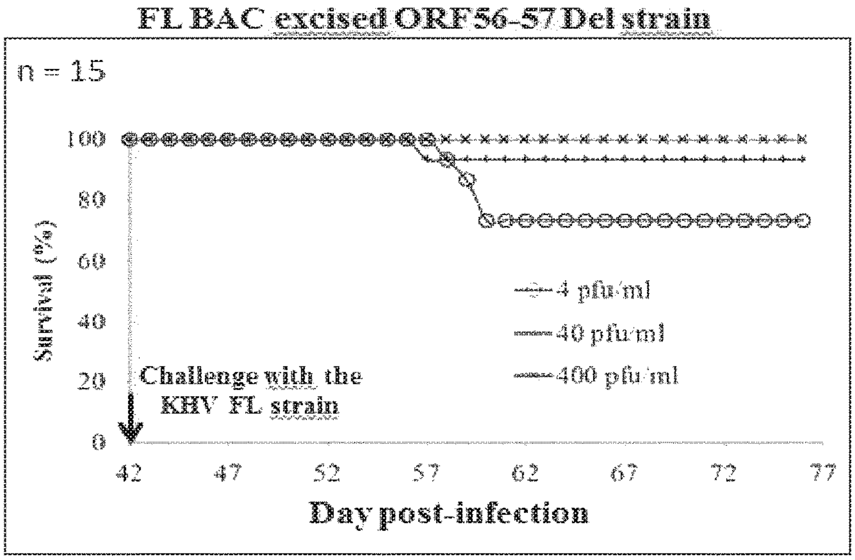
Figure 7G:
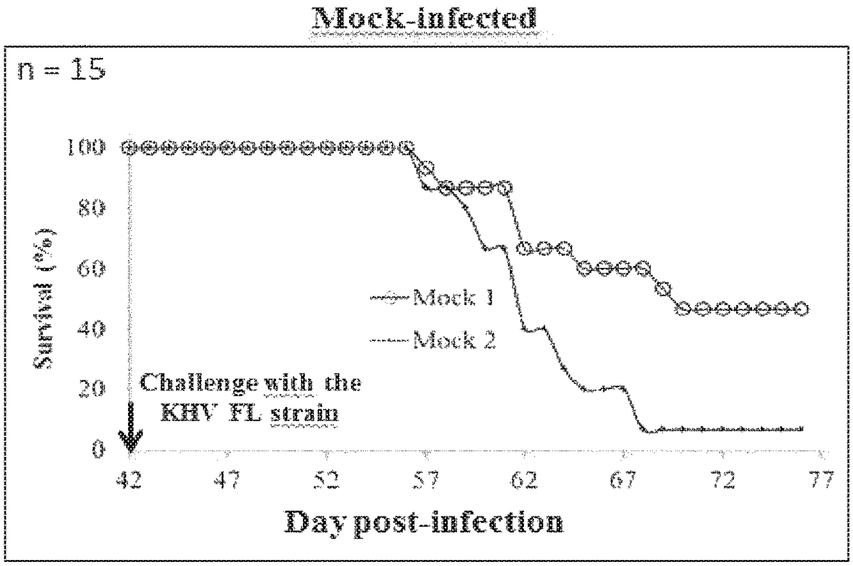
Figure 8A:
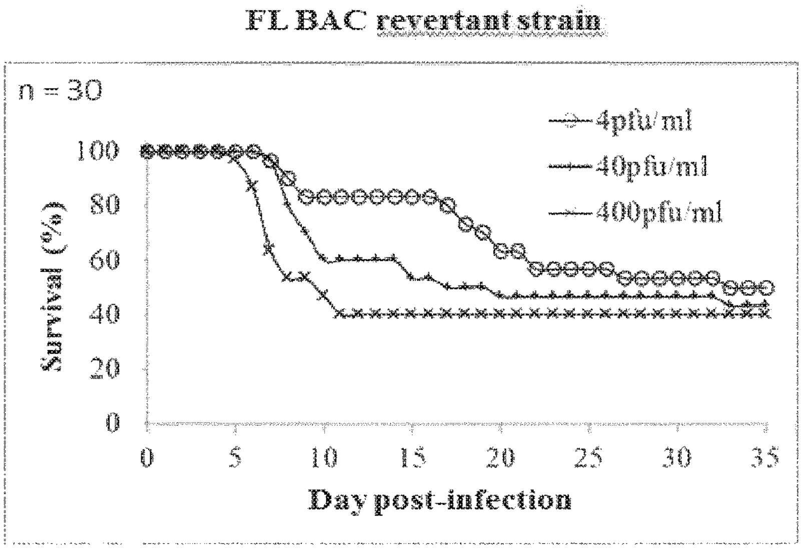
Figure 8B:
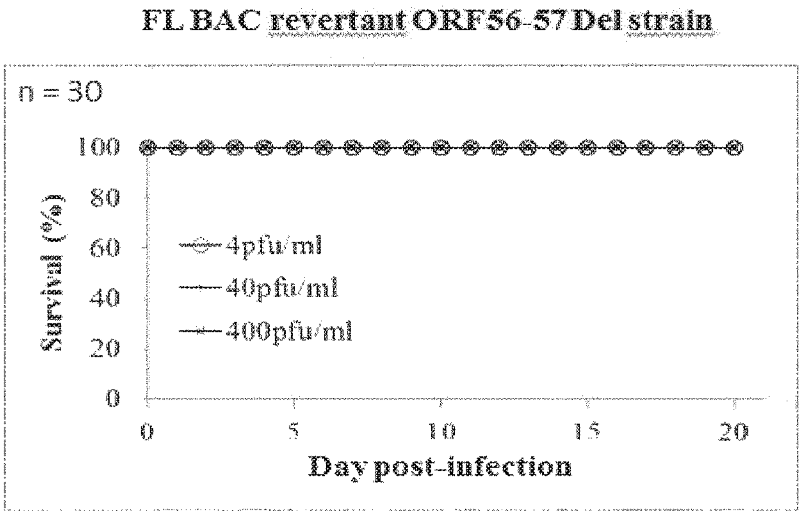
Figure 8C:
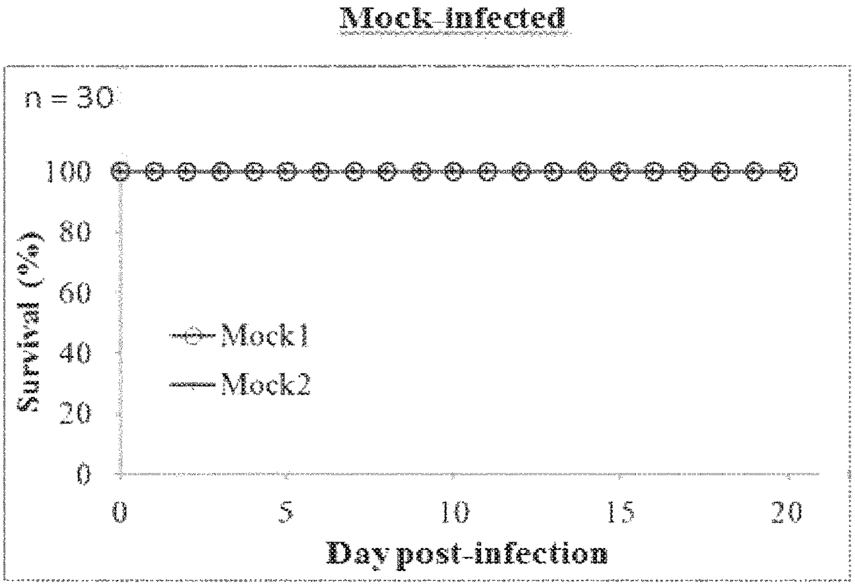
Figure 8D:
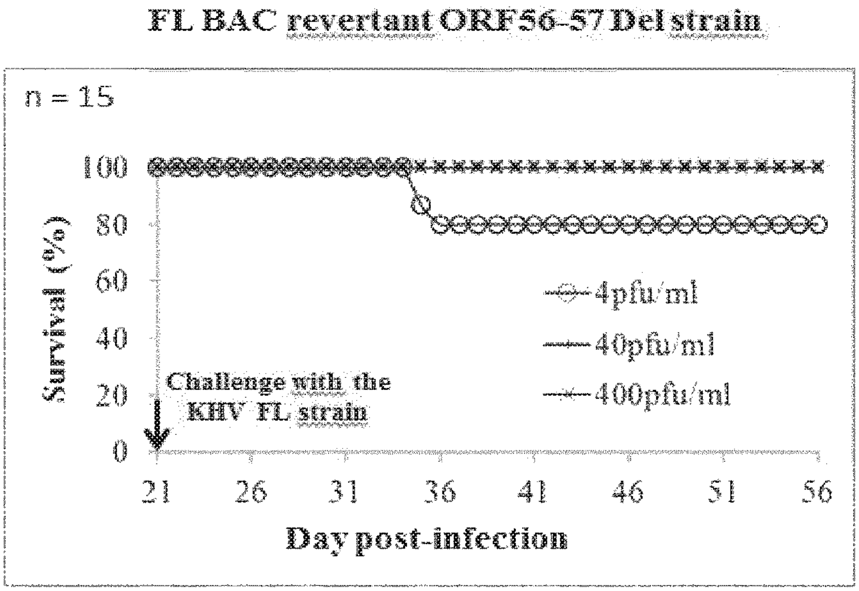
Figure 8E:
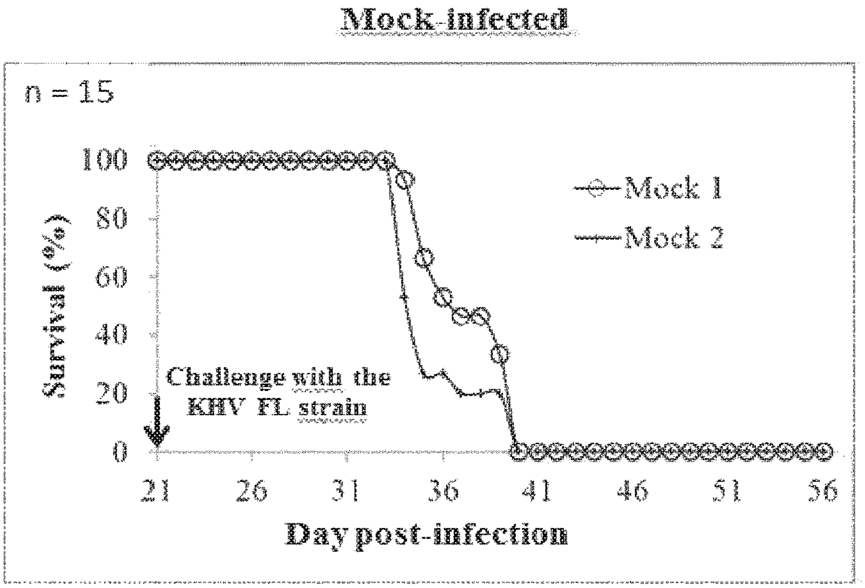
Figure 8F:
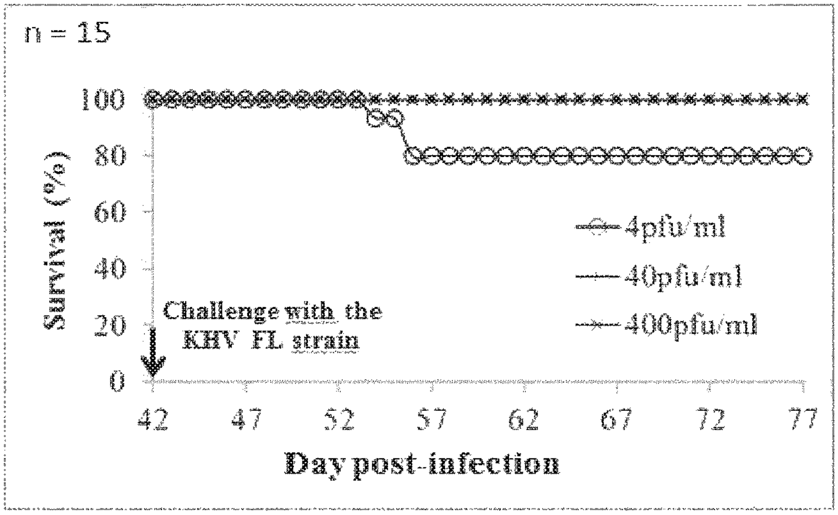
Figure 8G:
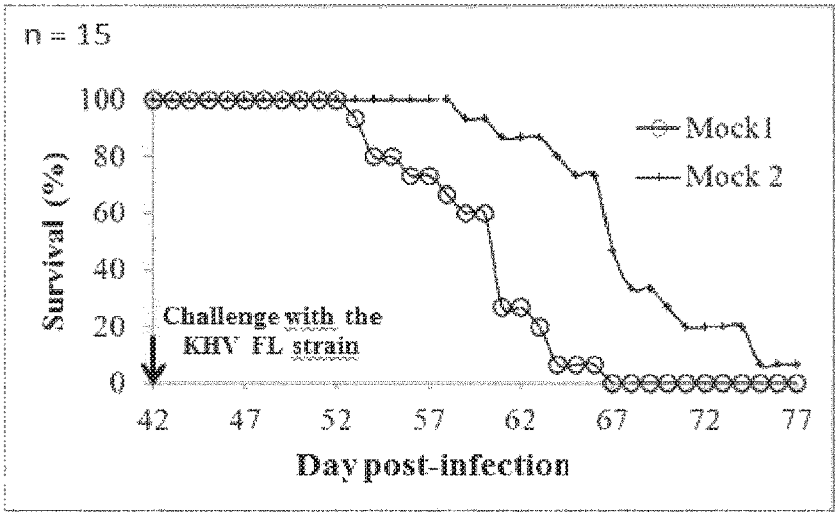

It also becomes clear from FIGS. 5E and F that a KHV ORF57 deletion mutant according to the invention is very suitable as an efficacious vaccine, especially when administered in a dose of 40 pfu/ml or higher.

The safety of the FL BAC excised ORF56 Del 1 galK (FIG. 6A) and the FL BAC excised ORF56 Del 2 galK (FIG. 6B) strains was tested as described in the examples (Safety tests) on common carp (7 months old, mean weight of 3.74 g, n=20). The FL BAC excised strain (FIG. 6C) and mock-infection (FIG. 6D) were used as positive and negative controls, respectively. Percentages of surviving carp are expressed according to days post-infection taking day 0 as the reference. As becomes clear from FIGS. 6A and B, ORF56 deletion mutants show a virulence that is roughly comparable with that of the control wild-type virus (Compare panels A and B to panel C).

As can be seen in FIGS. 7 and 8, a KHV carrying a deletion in both ORF57 and ORF56 shows a safety and efficacy profile that is comparable to that of KHV carrying a single ORF57 deletion.

REFERENCES

Aoki, T., Hirono, I., Kurokawa, K., Fukuda, H., Nahary, R., Eldar, A., Davison, A. J., Waltzek, T. B., Bercovier, H. & Hedrick, R. P. (2007). Genome sequences of three Koi herpesvirus isolates representing the expanding distribution of an emerging disease threatening Koi and common carp worldwide. *J Virol* 81, 5058-65.

Babic, N., Klupp, B. G., Makoschey, B., Karger, A., Flamand, A., Mettenleiter, T. C., 1996. Glycoprotein gH of pseudorabies virus is essential for penetration and propagation in cell culture and in the nervous system of mice. The Journal of general virology 77 (Pt 9), 2277-2285.

Borst, E. M., Hahn, G., Koszinowski, U. H. & Messerle, M. (1999). Cloning of the human cytomegalovirus (HCMV) genome as an infectious bacterial artificial chromosome in *Escherichia coli*: a new approach for construction of HCMV mutants. *J Virol* 73, 8320-9.

Costes, B., Fournier, G., Michel, B., Delforge, C., Raj, V. S., Dewals, B., Gillet, L., Drion, P., Body, A., Schynts, F., Lieffrig, F., Vanderplasschen, A., 2008. Cloning of the Koi herpesvirus genome as an infectious bacterial artificial chromosome demonstrates that disruption of the thymidine kinase locus induces partial attenuation in *Cyprinus carpio koi*. J Virol 82, 4955-4964.

Dewals, B., Boudry, C., Gillet, L., Markine-Goriaynoff, N., de Leval, L., Haig, D. M. & Vanderplasschen, A. (2006). Cloning of the genome of Alcelaphine herpesvirus 1 as an infectious and pathogenic bacterial artificial chromosome. *J Gen Virol* 87, 509-17.

Gillet, L., Daix, V., Donofrio, G., Wagner, M., Koszinowski, U. H., China, B., Ackermann, M., Markine-Goriaynoff, N. & Vanderplasschen, A. (2005). Development of bovine herpesvirus 4 as an expression vector using bacterial artificial chromosome cloning. *J Gen Virol* 86, 907-17.

Hedrick, R. P., Gilad, O., Yun, S. C., MCdowell, T. S., Waltzek, T. B., Kelley, G. O., Adkison, M. A. (2005). Initial isolation and characterization of a herpes-like virus (KHV) from Koi and common carp. *Bull. Fish. Res. Agen. Supplement* 2, 1-7.

Ilouze, M., Dishon, A. & Kotler, M. (2006). Characterization of a novel virus causing a lethal disease in carp and Koi. *Microbiol Mol Biol Rev* 70, 147-56.

Markine-Goriaynoff, N., Gillet, L., Karlsen, O. A., Haarr, L., Minner, F., Pastoret, P. P., Fukuda, M. & Vanderplasschen, A. (2004). The core 2 beta-1,6-N-acetylglucosaminyltransferase-M encoded by bovine herpesvirus 4 is not essential for virus replication despite contributing to post-translational modifications of structural proteins. *J Gen Virol* 85, 355-67.

Messerle, M., Crnkovic, I., Hammerschmidt, W., Ziegler, H. & Koszinowski, U. H. (1997). Cloning and mutagenesis of a herpesvirus genome as an infectious bacterial artificial chromosome. *Proc Natl Acad Sci USA* 94, 14759-63.

Morgan, R. W., Cantello, J. L. & McDermott, C. H. (1990). Transfection of chicken embryo fibroblasts with Marek's disease virus DNA. *Avian Dis* 34, 345-51.

Neukirch, M., Böttcher, K., Bunnajrakul, S. (1999). Isolation of a virus from Koi with altered gills. *Bull. Eur. Ass. Fish. Pathol.* 19, 221-224.

Ronen, A., Perelberg, A., Abramowitz, J., Hutoran, M., Tinman, S, Bejerano, I., Steinitz, M. & Kotler, M. (2003). Efficient vaccine against the virus causing a lethal disease in cultured *Cyprinus carpio*. Vaccine 21, 4677-84.

Schroder, C., Keil, G. M., 1999. Bovine herpesvirus 1 requires glycoprotein H for infectivity and direct spreading and glycoproteins gH(W450) and gB for glycoprotein D-independent cell-to-cell spread. The Journal of general virology 80 (Pt 1), 57-61.

Wagner, M., Ruzsics, Z. & Koszinowski, U. H. (2002). herpesvirus genetics has come of age. *Trends Microbiol* 10, 318-24.

Warden, C., Tang, Q., Zhu, H., 2011. Herpesvirus BACs: past, present, and future. Journal of biomedicine & biotechnology 2011, 124595.

Warming, S., Costantino, N., Court, D. L., Jenkins, N. A. & Copeland, N. G. (2005). Simple and highly efficient BAC recombineering using galK selection. *Nucleic Acids Res* 33, e36.

The invention claimed is:

1. A live, attenuated recombinant Koi herpesvirus (KHV) comprising a genome in which Open Reading Frame 56 (ORF 56) and Open Reading Frame 57 (ORF 57) are mutated, wherein the herpesvirus is capable of replication.

2. The herpesvirus of claim 1, wherein the mutation is selected from the group consisting of: one or more point mutations, insertions, partial deletions of open reading frames, full deletions of open reading frames, duplications, rearrangements, recombination, inversions and translocations.

3. The herpesvirus of claim 2, wherein the mutation comprises partial deletions of open reading frames.

4. The herpesvirus of claim 2, wherein the mutation comprises full mutations of open reading frames.

5. The herpesvirus of claim 1, which further comprises a bacterial artificial chromosome (BAC) vector sequence.

6. The herpesvirus of claim 5, wherein the BAC vector sequence is excised from the herpesvirus genome thereby leaving a heterologous DNA fragment at the excision site in the herpesvirus genome.

7. The herpesvirus of claim 1, further comprising at least one additional mutation in at least one additional gene.

8. The herpesvirus of claim 7, wherein the at least one additional gene is selected from the group consisting of a thymidine kinase gene, ORF 12, ORF16, ORF134, and ORF140.

9. The herpesvirus of claim 1, further comprising a heterologous DNA fragment.

10. A vector comprising the recombinant Koi herpesvirus (KHV) of claim 1.

11. An isolated cell comprising the recombinant Koi herpesvirus of claim 1.

12. A vaccine comprising either:

a. the live recombinant Koi herpesvirus of claim 1; or b. a recombinant Koi herpesvirus DNA comprising the genome of the live recombinant Koi herpesvirus.

13. The vaccine of claim 12, further comprising a pharmaceutically acceptable carrier.

14. A method of preventing or therapeutically treating a disease in fish caused by Koi herpesvirus (KHV) comprising administering the vaccine of claim 13.

15. An immunogenic composition comprising a pharmaceutically acceptable carrier and the live recombinant Koi herpesvirus of claim 1.

* * * * *